United States Patent [19]

Miller et al.

[11] Patent Number: 4,861,918

[45] Date of Patent: Aug. 29, 1989

[54] REACTIVATION OF HYDROFORMYLATION CATALYSTS

[75] Inventors: David J. Miller, Charleston; David R. Bryant, South Charleston; Ernst Billig, Charleston, all of W. Va.; Bernard L. Shaw, Leeds, England

[73] Assignee: Union Carbide Corporation, Danbury, Conn.

[21] Appl. No.: 231,510

[22] Filed: Aug. 12, 1988

[51] Int. Cl.$^4$ ............................................. C07C 45/50
[52] U.S. Cl. .................................... 568/454; 556/21; 568/492
[58] Field of Search ........................ 568/454; 556/21

[56] References Cited

U.S. PATENT DOCUMENTS

| | | | |
|---|---|---|---|
| 3,527,809 | 9/1970 | Pruett et al. | 568/454 |
| 3,555,098 | 1/1971 | Olivier et al. | 568/454 |
| 4,041,082 | 8/1977 | Onoda et al. | 568/454 |
| 4,196,096 | 4/1980 | Dawes et al. | 252/414 |
| 4,221,743 | 9/1980 | Halstead et al. | 568/454 |
| 4,242,284 | 12/1980 | Harris et al. | 568/454 |
| 4,260,828 | 4/1981 | Morrell et al. | 568/454 |
| 4,283,304 | 8/1981 | Bryant et al. | 252/413 |
| 4,297,239 | 10/1981 | Bryant et al. | 252/412 |
| 4,364,907 | 12/1982 | Barnes | 423/22 |
| 4,374,278 | 2/1983 | Bryant et al. | 568/454 |
| 4,429,161 | 1/1984 | Abatjoglou et al. | 568/14 |
| 4,473,655 | 9/1984 | Tsunoda et al. | 568/454 |
| 4,537,997 | 8/1985 | Kojima et al. | 568/454 |
| 4,547,595 | 10/1985 | Chang | 568/454 |
| 4,605,780 | 8/1986 | Billig et al. | 568/454 |
| 4,710,587 | 12/1987 | Bryant et al. | 568/454 |

FOREIGN PATENT DOCUMENTS 51-23212 2/1976 Japan .................................. 568/454

Primary Examiner—Werren B. Lone
Attorney, Agent, or Firm—Reynold J. Finnegan

[57] ABSTRACT

A process for improving the catalytic activity of a partially deactivated solubilized rhodium - tertiary organophosphine complex hydroformylation catalyst.

28 Claims, No Drawings

REACTIVATION OF HYDROFORMYLATION CATALYSTS

This invention relates to a process for improving the activity of partially deactivated rhodium-tertiary organophosphine complex hydroformylation catalysts.

BACKGROUND OF THE INVENTION

Processes for forming aldehyde products by the hydroformylation reaction of an olefinic compound with carbon monoxide and hydrogen in the presence of a rhodium-tertiary organophosphine complex hydroformylation catalyst are well known in the art. Of particular interest are those hydroformylation reactions designed to produce aldehydes at low pressures, such as disclosed, e.g. in U.S. Pat. Nos. 3,527,809; 4,148,830; 4,247,486; and 4,731,486.

Commercial experience has shown that, even in the substantial absence of extrinsic catalyst poisons, rhodium tertiary organophosphine complex catalysts lose activity (i.e. become partially deactivated) during the course of continued prolonged hydroformylation and such is commonly referred to as intrinsic deactivation. While it is difficult to ascertain the precise reasons for such loss in activity, such deactivation is believed to be due in a large part to the combined effects of a number of processing conditions, e.g. reaction temperature, reactant partial pressures, the phosphine ligand, the ligand to rhodium mole ratio, and rhodium concentration employed. Since the variables significant for such catalyst instability are also variables essential for the hydroformylation, obviously such deactivation can not be totally avoided although it can be controlled or minimized. However, eventually the activity of the catalyst will decrease to such a point that it is no longer desirable to operate the hydroformylation process and the catalyst will either have to be reactivated or discharged and replaced with fresh catalyst. Accordingly reactivation of such partially deactivated rhodium complex catalysts remains highly important to the state of the art in view of the high cost of rhodium as seen by the many various methods that have been proposed by the prior art for minimizing or preventing such deactivation and/or reactivating the partially deactivated rhodium complex hydroformylation catalyst.

For instance, U.S. Pat. No. 4,277,627 advocates that such deactivation can be reduced or substantially prevented by establishing, controlling and correlating the hydroformylation reaction conditions of temperature, carbon monoxide partial pressure and ligand to rhodium mole ratio to enhance stability of the catalyst via a stability factor formula.

U.S. Pat. No. 4,260,828 suggests utilizing the stability effect that alkyldiarylphosphine has on the rhodium catalyst and adjusting the reaction conditions to be more severe in order to regain the loss in catalyst productivity caused by such phosphine liquid.

U.S. Pat. No. 4,221,743 relates to a hydroformylation process wherein the rate of productivity of the process can be maintained at a desired rate by feeding oxygen during the hydroformylation reaction to the homogneous liquid phase composition of the reaction so as to maintain or increase the activity of the catalyst.

Japanese Patent Application Pub. No. 23,212/76 relates to maintaining or improving the rhodium catalytic activity of the hydroformylation reaction by removing the aldehyde from the reaction product mixture containing the catalyst and then treating all or a portion of the liquid catalyst medium with oxygen during recycle of the catalyst to the hydroformylation reaction. U.S. Pat. No. 4,041,082 relates to the same type of reactivation treatment save for employing carbon dioxide instead of oxygen.

U.S. Pat. No. 4,196,096 relates to a method for regenerating rhodium hydroformylation catalysts which comprises the steps of removing all or a portion of the inactive catalyst from the hydroformylation reaction, adjusting the aldehyde content so as to have at least one mole of aldehyde per mole of rhodium and ligand present and treating the catalyst with oxygen or an oxygen containing gas at a temperature below the boiling point of the aldehyde, removing any solid material formed during oxidation and adjusting the ligand to rhodium ratio as required for use in the hydroformylation reaction.

U.S. Pat. No. 4,605,780 advocates enhancing the activity of the rhodium complex hydroformylation catalyst by stopping the hydroformylation reaction and treating the catalyst containing hydroformylation reaction medium with oxygen to convert free alkyldiarylphosphine ligand to its corresponding phosphine oxide.

U.S. Pat. No. 4,297,239 advocates that partially deactivated rhodium tertiary organophosphine complex catalysts can be regenerated or reactivated by forming a rhodium complex concentrate via distillation of the hydroformylation reaction medium, followed by oxidation and/or washing of the concentrate if desired, said concentrate being employable as a source of reactivated rhodium for the catalyst of any hydroformylation process.

U.S. Pat. No. 3,555,098 suggests maintaining or improving the rhodium catalytic activity of a hydroformylation reaction by washing all or a portion of a liquid medium containing the catalyst with an aqueous solution, e.g. an aqueous alkaline solution to remove by product acid, e.g. carboxylic acid, formed during hydroformylation by oxidation of the aldehyde which may have been due to oxygen contamination of the reactant gas system.

U.S. Pat. No. 4,283,304 advocates improving the activity and increasing the life span of the rhodium complex catalyst of a continuous hydroformylation process (e.g. column 21) by removing in situ produced alkyldiarylphosphine ligand from the hydroformylation reaction medium by treating said medium with an alpha, beta unsaturated compound (as seen e.g. in column 10) such as a halide, carboxylic acid or anhydride of the carboxylic acid (e.g. vinyl chloride, maleic acid, and maleic anhydride, etc.), allowing an aqueous mixture of said treated medium to separate into two phases and separating the aqueous phase which contains the solubilized reaction products of the alkyldiarylphosphine present and said alpha, beta unsaturated compound from the non aqueous phase containing the rhodium complex catalyst, which non aqueous phase can be washed with any suitable aqueous alkaline solution e.g. sodium bicarbonate and water if desired. The non aqueous containing catalyst solution can then be reemployed in the hydroformylation process.

While all of the above prior art treatment procedures suggested to effect catalyst reactivity may have certain individual beneficial aspects, there is still a need in the art for a method which permits restoration of such partially deactivated rhodium catalyst activity under simple mild conditions and without complicated handling or processing procedures and without introducing unduly adverse side reactions.

DISCLOSURE OF THE INVENTION

It has now been discovered that the activity of a rhodium-tertiary organophosphine complex hydroformylation catalyst that has become partially deactivated as a result of its employment in a hydroformylation reaction directed to producing aldehyde products by reacting an olefinic compound, carbon monoxide and hydrogen in the presence of a hydroformylation reaction medium containing a solubilized rhodium-tertiary organophosphine complex catalyst, can be improved by treating the solubilized partially deactivated rhodium-tertiary phosphine complex catalyst with certain organic reagents and eliminating any hydroformylation catalytic inhibitor formed by said treatment.

Thus it is an object of this invention to provide a process for improving the catalytic activity of such partially deactivated rhodium-tertiary organophosphine complex hydroformylation catalysts. Other objects and advantages of this invention will become readily apparent from the following description and appended claims.

Accordingly a generic aspect of this invention can be described as a process for improving the catalytic activity of a partially deactivated solubilized rhodium-tertiary organophosphine complex hydroformylation catalyst, which comprises (1) mixing under non hydroformylating conditions, a liquid medium containing said solubilized partially deactivated complex catalyst, with an organic reagent selected from the group consisting of (a) alkyne compounds having the formula $R-C\equiv C-CH_2-X$, (b) alkene compounds having the formula $(R^1)(R^2)C=C(R^3)-CH_2-X$, (c) diketene, (d) methyl halides, (e) methyl sulfonates, (f) propiolate compounds having the formula $HC\equiv C-C(O)OR^{14}$, and (g) oxide compounds having the formula

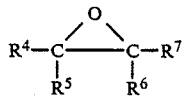

wherein X represents a radical selected from the group consisting of halogen atoms, a carboxylate radical of the formula $-OC(O)R^8$, a sulfonate radical of the formula $-OSO_2R^8$ and a phosphonium radical of the formula $[-P^+(R^8)_3][Y-]$; wherein $R^8$ in the above formulae for X, each individually represent a monovalent hydrocarbon radical having from 1 to 18 carbon atoms selected from the group consisting of alkyl, aryl, aralkyl, alkaryl and cycloalkyl radicals and wherein Y represents an anion; and wherein each R, $R^1$, $R^2$, $R^3$, $R^4$, $R^5$, $R^6$, $R^7$, and $R^{14}$ radical individually represents a radical selected from the group consisting of hydrogen and a monovalent hydrocarbon radical having from 1 to 18 carbon atoms (e.g. alkyl, aryl, alkaryl, aralkyl and cycloalkyl radicals), with the following provisos: that $R^8$ in the above carboxylate formula can also be hydrogen; that $R^2$ and $R^3$ in the above formula for the alkene compounds can also be bonded together to form a five or six membered heterocyclic ring or monocyclic hydrocarbon ring along with the $C=C$ group shown in said formula; and wherein any two of said $R^4$, $R^5$, $R^6$ and $R^7$ groups in the above formula for the oxides can be bonded together to form a five or six membered monocyclic hydrocarbon ring along with the $C-C$ group shown in said formula; to obtain an organic reagent treated solubilized rhodium-tertiary organophosphine complex product; and (2) eliminating from said product, any hydroformylation catalytic inhibitor formed by said Step (1), to obtain a rhodium-tertiary organophosphine complex hydroformylation catalyst that is more catalytically active than said partially deactivated rhodium-tertiary organophosphine complex hydroformylation catalyst.

DESCRIPTION OF THE PREFERRED EMBODIMENTS

As noted above the subject invention resides in the discovery that the catalytic activity of a rhodium-tertiary organophosphine complex hydroformylation catalyst which has become partially deactivated as a result of its continued employment in a hydroformylation reaction directed to producing aldehyde products by reacting an olefinic compound, carbon monoxide and hydrogen in the presence of a hydroformylation reaction medium containing solubilized rhodium-tertiary organophosphine complex catalyst can be improved by the process of this invention.

Thus, the solubilized partially deactivated rhodium-tertiary organophosphine complex catalyst contained in the liquid medium treated in accordance with this invention can be any such catalyst complex resulting from a hydroformylation process directed to producing aldehydes by hydroformylating an olefinic compound with carbon monoxide and hydrogen in the presence of a rhodium-tertiary organophosphine complex catalyst and which process has been operated to the extent that the originally employed catalyst complex has become at least partially deactivated, i.e. a catalyst which has become less reactive then its original counterpart. The extent of such catalytic deactivation (or catalyst activity) may be determined at any given time by comparing the hydroformylation conversion rate to aldehyde product based on such catalyst to the conversion rate obtained using fresh catalyst.

Moreover the solubilized partially deactivated rhodium-tertiary organophosphine complex catalysts that may be reactivated in accordance with this invention can be present in any suitable liquid medium which would not unduly adversely affect the basic purpose of this invention. For example such liquid mediums may consist of only the partially deactivated rhodium-tertiary organophosphine complex catalyst and a solvent for said complex catalyst. More preferably such liquid mediums may comprise all or any part of the hydroformylation reaction medium and/or all or any part of the liquid catalyst recycle medium of the corresponding hydroformylation process that produced the partially deactivated rhodium-tertiary organophosphine complex catalyst.

As pointed out by the above prior art, methods for hydroformylating olefinic compounds to produce aldehydes with a rhodium-tertiary organophosphine complex catalyst are well known in the art. Thus it should be clear that the particular hydroformylation process for producing aldehydes from an olefinic compound, as well as the reaction conditions and ingredients of said hydroformylation process, which serve as a means for furnishing the solubilized partially deactivated rhodium-tertiary organophosphine complex catalyst containing liquid medium starting material of the present invention, are not critical features of the present invention.

In general preferred hydroformylation processes comprise reacting an olefinic compound with carbon monoxide and hydrogen in a reaction vessel and in the presence of a hydroformylation reaction medium comprising aldehyde products, a solubilized rhodium-tertiary organophosphine complex catalyst, free tertiary organophosphine ligand and a solvent for said catalysts. In continuous hydroformylation reactions aldehyde products are constantly being removed, the rhodium-tertiary organophosphine complex catalyst either remaining in the hydroformylation reaction medium in the reactor as in the case of a gas recycle operation (e.g. U.S. Pat. No. 4,247,486), or being recycled back to the reactor after removal of some of the liquid reaction medium from the reactor and separation of aldehyde product therefrom, as in the case of a liquid catalyst recycle operation (e.g. U.S. Pat. Nos. 4,148,830 and 4,731,486).

Thus the "liquid medium" starting material as employed herein preferably means any liquid medium comprising a partially deactivated rhodium-tertiary organophosphine complex hydroformylation catalyst, free tertiary organophosphine ligand, and a solvent for said complex catalyst and free ligand, and such liquid mediums may be derived from any conventional corresponding hydroformylation process.

Accordingly the liquid medium starting materials employable herein preferably contain at least some amount of three different main ingredients or components, i.e., the partially deactivated rhodium-tertiary organophosphine complex hydroformylation catalyst, free tertiary organophosphine ligand, and a solvent for said complex catalyst and said free ligand, said ingredients preferably corresponding to those employed and/or produced by the hydroformylation process from whence the liquid medium starting material may be derived.

Preferably said liquid medium starting materials also contain at least some amount of the aldehyde product corresponding to the desired aldehyde product of the hydroformylation process from whence such liquid mediums may be derived, although it may be possible, to remove all of such aldehyde product prior to treating the liquid medium by the process of this invention. Of course it is to be further understood that the liquid medium starting materials of this invention can contain minor amounts of additional ingredients such as those which have either been deliberately employed in the hydroformylation process or formed in situ during said process. Examples of such additional ingredients that can also be present include unreacted olefin starting material, and in situ formed type products, such as unreacted isomerized olefin, hydrogenated olefin e.g. corresponding saturated hydrocarbons or paraffin by-products); in situ type by products derived from the aldehyde products, such as high boiling aldehyde condensation by products (as described e.g. in U.S. Pat. Nos. 4,148,830 and 4,247,486) and in situ type alkyl substituted phosphine ligand by-product such as described e.g. in U.S. Pat. No. 4,260,828). Moreover, the liquid medium starting materials of this invention are preferably essentially non-aqueous, as a result of having been derived from an essentially non-aqueous, homogeneous hydroformylation process. However, it is to be understood that such liquid mediums could also contain water, e.g., as a result of having been derived from an aqueous hydroformylation process employing an aqueous solution of a rhodium-ionic tertiary organophosphine ligand complex catalyst.

Accordingly it should be sufficient for the purpose of this invention to understand that whatever compounds are present during the hydroformylation process, from which the liquid medium starting materials of this invention can be derived, may also be correspondingly present in said liquid medium starting materials of this invention.

Thus the particular partially deactivated rhodium-tertiary organophosphine complex hydroformylation catalyst, present in the liquid medium starting material to be treated in accordance with this invention can be any such corresponding conventional rhodium hydroformylation catalyst which has been employed in a hydroformylation reaction to the extent that it has become partially deactivated. Accordingly the particular partially deactivated rhodium-tertiary organophosphine complex hydroformylation catalyst, as well as its amount in a given liquid medium starting material of this invention may obviously correspond to and merely be dependent upon the particular rhodium-tertiary organophosphine complex catalyst employed in and/or formed under the reaction conditions of the particular hydroformylation reaction from whence the liquid medium starting material to be treated according to this invention has been derived. For example illustrative rhodium-tertiary organophosphine complex catalysts and hydroformylation reactions, include e.g. those disclosed in U.S. Pat. Nos. 3,527,809; 3,959,385; 4,148,830; 4,247,486; 4,248,802; 4,283,562; 4,399,312; 4,400,548; 4,482,749; 4,491,675; 4,593,127; 4,633,021; 4,716,250; 4,731,486; European Patent Applications Publication Nos. 163,234 (published May, 1985) and 216,315 (published April, 1987); PCT Application, Publication No. WO 80/01690 (published August, 1980); and the like, the entire disclosures of which are incorporated herein by reference thereto. Of course mixtures of different catalysts and organophosphine ligands can be employed if desired. Moreover, as noted in said references, the hydroformylation processes are generally and preferably carried out in the presence of free tertiary organophosphine ligand i.e. ligand that is not complexed with the rhodium complex catalyst employed. While it is generally preferred that the free ligand be the same as the tertiary organophosphine ligand of the rhodium-tertiary organophosphine complex catalyst, such is not necessary. Accordingly it is to be understood that in the case of the rhodium-tertiary organophosphine complex catalyst, as well as in the case of the free tertiary organophosphine ligand any conventional tertiary organophosphine ligand, heretofore advanced for such hydroformylation purposes, such as disclosed e.g. by the above mentioned references, can be employed herein.

Accordingly illustrative tertiary organophosphines that may be employed, either as the free ligand and/or as the ligand of the rhodium complex catalyst, include e.g. trialkylphosphines, alkyldiarylphosphines, dialkylarylphosphines, dicycloalkylarylphosphines, cycloalkyldiarylphosphines, triaralkylphosphines, tricycloalkylphosphines, and triarylphosphines, alkyl and/or aryl bisphosphines and bisphosphine mono oxides, as well as ionic triorganophosphines containing at least one ionic moiety selected from the group consisting of the salts of sulfonic acid, of carboxylic acid, of phosphonic acid and of quaternary ammonium compounds, and the like. Of course any of the hydrocarbon radicals of such tertiary non-ionic and ionic organophosphines may be substituted if desired, with any suitable substituent that does not unduly adversely affect the desired result of the hydroformylation process or this invention. Illustrative substituents that may be on the hydrocarbon radicals in addition of course to corresponding hydrocarbon radicals such as alkyl, aryl, aralkyl, alkaryl and cyclohexyl substitutents, may include for example silyl radicals such as —Si($R^9$)$_3$; amino radicals such as —N($R^9$)$_2$; acyl radicals such as —C(O)$R^9$, acyloxy radicals such as —OC(O)$R^9$; amido radicals such as —CON($R^9$)$_2$ and —N($R^9$)CO$R^9$; sulfonyl radicals such as —SO$_2R^9$, alkoxy radicals such as —O$R^9$; thionyl radicals such as —S$R^9$, phosphonyl radicals such as —P(O)($R^9$)$_2$, as well as, halogen, nitro, cyano, trifluoromethyl, hydroxy radicals, and the like, wherein each $R^9$ individually represents the same or different monovalent hydrocarbon radical having from 1 to 18 carbon atoms (e.g., alkyl, aryl, aralkyl, alkaryl and cyclohexyl radicals), with the proviso that amino substituents such as —N($R^9$)$_2$, each $R^9$ taken together can also represent a divalent bridging group that forms a heterocyclic radical with the nitrogen atom, and in amido substituents such as —C(O)N($R^9$)$_2$ and —N($R^9$)CO$R^9$ each $R^9$ bonded to N can also be hydrogen. Of course it is to be understood that any of the substituted or unsubstituted hydrocarbon radicals groups that make up a particular given tertiary organophosphine may be the same or different.

Such tertiary organophosphines and corresponding rhodium-tertiary organophosphine complex catalysts and/or methods for their preparation are well known as seen e.g. by the above mentioned references. Preferred tertiary organophosphines are non-ionic and ionic phosphines, such as non-ionic triorganophosphines having the formula ($R^{10}$)$_3$P wherein each $R^{10}$ individually represents a monovalent hydrocarbon radical containing from 1 to 18 carbon atoms selected from the alkyl, aralkyl, alkaryl, cycloalkyl and aryl radicals, as disclosed e.g., in U.S. Pat. Nos. 3,527,809 and 4,283,562, and the like; and ionic triorganophosphines having the formula

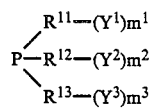

wherein $R^{11}$, $R^{12}$, and $R^{13}$ each individually represent a monovalent hydrocarbon radical containing from 1 to 18 carbon atoms selected from the group consisting of alkyl, aryl, alkaryl, aralkyl and cycloalkyl radicals, wherein $Y^1$, $Y^2$, and $Y^3$ each individually represent an ionic radical of overall neutral charge selected from the group consisting of —SO$_3$M, —PO$_3$M, and —COOM wherein M represents an inorganic (e.g., alkali or alkali earth metal) or organic (e.g., quaternary ammonium) radical, and —N($R^{13}$)$_3Y^4$ wherein each $R^{13}$ represents hydrogen or a monovalent hydrocarbon radical containing from 1 to 18 carbon atoms selected from the group consisting of alkyl, aryl, alkaryl, aralkyl and cycloalkyl radicals and wherein $Y^4$ represents an inorganic or organic anion; wherein $m^1$, $m^2$ and $m^3$ are integers each having a value of from 0 to 3, at least one of $m^1$, $m^2$, and $m^3$ having a value of at least one, as e.g. in U.S. Pat. Nos. 4,248,802; 4,399,312; 4,633,021; 4,668,824; 4,716,250; and 4,731,486; EPC Patent Application Publication Nos. 163,234 and 216,315; and the like, especially U.S. Pat. No. 4,731,486.

Among the more preferred tertiary organophosphines are triphenylphosphine, propyldiphenylphosphine, t-butyldiphenylphosphine, n-butyldiphenylphosphine, n-hexyldiphenylphosphine, cyclohexyldiphenylphosphine, dicyclohexylphenylphosphine, tricyclohexylphosphine, tribenzylphosphine as well as the alkali and alkaline earth metal salts of sulfonated triphenylphosphines, e.g., of (tri-m-sulfophenyl) phosphine and of (m-sulfophenyl) diphenyl phosphine and the like. The most preferred ligands are triphenylphosphine (TPP), and the sodium salt of 3-(diphenylphosphino) benzene sulfonic acid (TPPMS-Na), while the most preferred catalysts are a rhodium-TPP and a rhodium-TPPMS-Na complexes.

As seen by the above mentioned hydroformylation references, the rhodium complex catalysts are generally considered as consisting essentially of rhodium complexed with carbon monoxide and tertiary organophosphine (generally corresponding to the free tertiary organophosphine ligand also normally present in the reaction medium). The catalyst terminology "consisting essentially of" is not meant to exclude, but rather include the possibility of any other ligand or any anion, which does not unduly adversely affect the hydroformylation process, complexed with the rhodium such as hydrogen which is also a ligand in addition to the carbon monoxide and tertiary organophosphine, the hydrogen being derived from the hydrogen gas of the hydroformylation reaction, if not already present in the catalyst precursor. Such hydroformylation catalysts may be formed in situ during the hydroformylation reaction or preformed by methods known in the art. For example preformed rhodium hydridocarbonyl-tris (tertiary organophosphines) may be introduced into the reaction medium of the hydroformylation reaction. Alternatively rhodium catalyst precursors such as rhodium carbonyl tertiary organophosphine acetylacetonates, Rh$_2$O$_3$, Rh$_4$(CO)$_{12}$, Rh$_6$(CO)$_{16}$, Rh(NO$_3$)$_3$ or rhodium dicarbonyl acetylacetonate, and the like, may be introduced into the reaction medium of the hydroformylation reaction. In any event an active rhodium complex hydroformylation catalyst is present in the hydroformylation reaction medium under the conditions of hydroformylation.

However, it is to be noted that the successful practice of this invention does not depend and is not predicated on any explanation as to the exact structure or nature of the active rhodium complex catalyst species or as to the exact structure or nature of the partially deactivated rhodium hydroformylation catalyst species formed during the hydroformylation. Indeed such exact structures are not known with certainty. Clearly for the purpose of understanding this invention, it is sufficient to simply point out that the partially deactivated rhodium-tertiary organophosphine complex hydroformylation catalysts present in the liquid medium starting materials of this invention can be any such complex partially deactivated catalyst mixture resulting from the use of a corresponding rhodium-tertiary organophosphine complex catalyst in the hydroformylation reaction medium of the hydroformylation process from whence the particular liquid medium starting material employable in the process of this invention is derived.

The amount of the partially deactivated rhodium-tertiary phosphine complex hydroformylation catalyst present in the liquid medium starting materials of this invention may range from about one part per million (ppm), up to about 50,000 parts per million (ppm) or more, calculated as rhodium metal. In general the amount of such partially deactivated rhodium complex catalyst present in the liquid medium starting material of this invention preferably corresponds to the amount of the rhodium-tertiary organophosphine complex hydroformylation catalyst employed in the hydroformylation reaction medium of the hydroformylation process from whence the liquid medium starting material may be derived and such amounts are commonly expressed in terms of the amount of rhodium present calculated as rhodium metal. In the more preferred low pressure non-aqueous hydroformylation processes, rhodium hydroformylation concentrations preferably do not exceed 500 ppm, calculated as rhodium metal, with concentrations of from about 50 up to 300 ppm, calculated as rhodium metal being even more preferred. Of course the liquid medium starting materials of this invention may contain higher concentrations of rhodium than present in the hydroformylation reaction medium, and such may be readily obtained e.g. simply by concentrating the rhodium catalyst containing hydroformylation medium prior to employing same as the liquid medium starting material of this invention. Such concentration procedures e.g., may range from merely removing some of the aldehyde product on up to preparing very viscous rhodium containing concentrates such as taught e.g. in U.S. Pat. No. 4,297,239. Rhodium concentrations in the range of from about 5 to about 10,000 ppm, and more preferably from about 10 to about 1000 ppm, of rhodium, calculated as rhodium metal, should be sufficient for most hydroformylation process and such corresponding amounts are preferably present in the liquid medium starting materials of this invention.

As noted above the tertiary organophosphine ligands defined herein are employed in this invention as both the ligand of the rhodium-tertiary organophosphine complex catalyst as well as, the free tertiary phosphine ligand that is also present in the liquid medium starting materials of this invention. In a given situation such rodium-phosphine complexes and free phosphine ligands of course will correspond to those employed in the hydroformylation process from which said liquid mediums may be derived. In addition, it is to be understood that while the tertiary organophosphine of the rhodium complex catalyst and free tertiary organophosphine ligand present in the reaction medium of a given hydroformylation process are normally the same, different tertiary organophosphine ligands, as well as, mixtures of two or more different tertiary organophosphine ligands may be employed for each individual purpose, if desired. As in the case with the amounts of rhodium complex catalyst employed, the amount of free tertiary organophosphorus ligand present in a given liquid medium starting material of this invention will in general correspond to that amount of corresponding free ligand present in the hydroformylation process from which said liquid medium may be derived. For instance, since the hydroformylation process may be carried out in any excess amount of free tertiary organophosphine ligand desired e.g., at least one mole of free tertiary organophosphine ligand per mole of rhodium present in the reaction medium, the amount of free tertiary organophosphine ligand present in a given liquid medium starting material of this invention can also be any corresponding excess amount e.g., at least one mole of free tertiary organophosphine ligand per mole of rhodium metal present in the liquid medium starting material.

In general an amount of free tertiary organophosphine ligand of from about 2 to about 300, and preferably from about 5 to about 200 moles per mole of rhodium metal present in the reaction medium should be suitable for most hydroformylation processes. Accordingly, corresponding amounts of free tertiary organophosphine ligand may be present in the liquid medium starting materials of this invention.

The liquid medium starting materials of this invention also contain a solvent generally corresponding to that employed for solubilizing the rhodium-tertiary organophosphine complex catalyst and free tertiary organophosphine ligand present in the reaction medium of the hydroformylation process from which said liquid medium starting materials of this invention may be derived. Any suitable solvent which does not adversely interfere with the intended hydroformylation process of this invention can be employed. Such solvents are well known in the art and encompass both polar and nonpolar organic solvents, as well as water. Illustrative suitable organic solvents include those described e.g. in U.S. Pat. Nos. 3,527,809; 4,148,830; and 4,731,486, as well as water or aqueous solvent mixtures such as described in U.S. Pat. No. 4,248,802. Of course, mixtures of one or more different solvents may be employed if desired. Organic solvents are preferred. Moreover, when organic solvent soluble non-ionic tertiary organophosphine ligands are involved, the preferred solvents are aldehyde compounds corresponding to the aldehyde products of the hydroformylation process and/or higher boiling aldehyde condensation by-products such as described e.g. in U.S. Pat. Nos. 4,148,830 and 4,247,486. When organic solvent soluble ionic tertiary organophosphine ligands are involved, such as ligands containing only one ionic moiety, the preferred solvents are polar organic solubilizing agents selected from the group consisting of an alkylene oxide oligomer having an average molecular weight of at least 150, an organic nonionic surfactant mono-ol having an average molecular weight of at least 300 and a polar organic compound having a molecular weight of less than 150 and a Hildebrand solubility value of at least 10, as well as mixtures thereof, such as described e.g. in U.S. Pat. No. 4,731,486. Polar solubilizing agents such as water and aqueous mixtures, are preferred when ionic tertiary organophosphine ligands containing more than one ionic moiety, are involved. Preferred polar organic solvents for organic solvent-soluble ionic tertiary phosphine ligands and rhodium-ionic tertiary phosphine complex catalysts, wherein the ionic phosphine contains only one ionic moiety are amides, sulfoxides and sulfones, and mixtures thereof, the more preferred polar organic solubilizing agents being amides, for instance, N-methylpyrolidone. The amount of solvent present in the liquid medium starting materials need only be that amount sufficient to solubilize the partially deactivated rhodium-tertiary organophosphine complex catalyst and free ligand present in said liquid medium. In general such amounts of solvent may correspond to those amounts of solvent present in the reaction medium or catalyst containing recycle medium of the hydroformylation process from whence the liquid medium starting materials of this invention may be derived.

Thus in general the amount of organic solvent present in the liquid medium starting materials of this invention may range from about 5 to about 95 parts by weight based on the total weight of said liquid medium starting material. The preferred polar organic solvents for organic solvent soluble ionic tertiary organophosphines and rhodium-ionic tertiary organophosphine complex catalysts wherein the ionic phosphine contains only one ionic moiety are preferably present in hydroformylation reaction mediums in an amount not greater than 60 percent by weight of said medium.

Finally as noted above, the liquid medium starting materials of the process of this invention also preferably contain at least some amount of aldehyde product corresponding to the aldehyde product obtained by the hydroformylation process from whence said liquid medium starting materials may be derived. Such aldehydes may contain from 3 to 31 carbon atoms and encompass the corresponding hydroformylation aldehyde products obtained upon hydroformylating olefinic compounds containing from 2 to 30 carbon atoms. Such olefinic compounds can be terminally or internally unsaturated and be of straight-chain, branched chain or cyclic structures, as well as be olefin mixtures, such as obtained from the oligomerization of propene, butene, isbutene, etc., (such as so called dimeric, trimeric or tetrameric propylene, codibutylene, and the like, as disclosed e.g. in U.S. Pat. Nos. 4,518,809 and 4,528,403). Moreover such olefinic compounds may further contain one or more ethylenic unsaturated groups and of course mixtures of two or more different olefinic compounds may be employed as the starting hydroformylation material if desired. Further such olefinic compounds and the corresponding aldehyde products derived therefrom may also contain one or more groups or substituents which do not unduly adversely affect the hydroformylation process or the process of this invention such as described e.g., in U.S. Pat. Nos. 3,527,809; 4,731,486 and the like.

Illustrative olefinic unsaturated compounds are alpha-olefins, internal olefins, alkyl alkenoates, alkenyl alkanoates, alkenyl alkyl ethers, alkenols, and the like e.g., ethylene, propylene, 1-butene, 1-hexene, 1-octene, 1-nonene, 1-decene, 1-undecene, 1-tridecene, 1-tetradecene, 1-pentadecene, 1-hexadecene, 1-heptadecene, 1-octadecene, 1-nonadecene, 1-eicosene, 2-butene, 2-methyl propene (isobutylene), 2-pentene, 2-hexene, 2-heptene, propylene dimers, propylene trimers, propylene tetramers, 2-ethyl hexene, 2-octene, styrene, 3-phenyl-1-propene, 1,4-hexadiene, 1,7-octadiene, 3-cyclohexyl 1-butene, allyl butyrate, methyl methacrylate, vinyl ethyl ether, vinyl methyl ether, allyl ethyl ether, n-propyl-7-octenoate, 3-butenenitrile, 5-hexenamide, 4-methyl styrene, 4-isopropyl styrene, 4-tert-butyl styrene, alpha methyl styrene,4-tert butyl-alpha-methyl styrene, 1,3-diisopropenyl-benzene, eugenol, iso-eugenol, safrole, iso-safrole, anethol, 4-allylanisole, indene, limonene, beta-pinene, dicyclopentadiene, cyclooctadiene, camphene, linalool, and the like.

Accordingly illustrative aldehyde products include e.g, propionaldehyde, n-butyraldehyde, isobutyraldehyde, n-valeraldehyde, 2-methyl 1-butyraldehyde, hexanal, 2-methyl valeraldehyde, heptanal, 2-methyl 1-hexanal, octanal, 2-methyl 1-heptanal, nonanal, 2-methyl-1-octanal, 2-ethyl 1-heptanal, 3-propyl 1-hexanal, decanal, 2-methyl-1-nonanal, undecanal, 2-methyl 1-decanal, dodecanal, 2-methyl 1-undecanal, tridecanal, 2-methyl-1-tridecanal, 2-ethyl 1-dodecanal, 3-propyl-1-undecanal, pentadecanal, 2-methyl-1-tetradecanal, hexadecanal, 2-methyl-1-pentadecanal, heptadecanal, 2-methyl-1-hexadecanal, octadecanal, 2-methyl-1-heptadecanal, nonadecanal, 2-methyl-1-octadecanal, 2-ethyl 1-heptadecanal, 3-propyl-1-hexadecanal, eicosanal, 2-methyl-1-nonadecanal, heneicosanal, 2-methyl-1-eicosanal, tricosanal, 2-methyl-1-docosanal, tetracosanal, 2-methyl-1-tricosanal, pentacosanal, 2-methyl-1-tetracosanal, 2-ethyl 1-tricosanal, 3-propyl-1-docosanal, heptacosanal, 2-methyl-1-octacosanal, nonacosanal, 2-methyl-1-octacosanal, hentriacontanal, 2-methyl-1-triacontanal, and the like.

Of course it is understood that the aldehyde product of an alpha olefin will normally be a mixture of the normal straight-chain aldehyde and its branched chain aldehyde isomer obtained upon hydroformylating said olefin. Moreover, mixtures of totally different aldehyde products can be present in the liquid medium starting materials employable in this invention, e.g., when such liquid mediums are derived from a process that hydroformylates mixtures of totally different olefinic compounds, such as e.g., mixtures of alpha olefins and internal olefins or mixtures of two different alpha olefins. The preferred aldehyde products present in the hydroformylation reaction product compositions employable in this invention are those derived from hydroformylating alpha olefins, internal olefins and mixtures of such alpha and internal olefins.

The more preferred olefin starting materials are alpha olefins having from 2 to 20 carbon atoms and more preferably from 3 to 14 carbon atoms. Of course it is to be understood that commercial alpha olefins containing 4 or more carbon atoms may contain minor amounts of corresponding internal olefins and/or their corresponding saturated hydrocarbon and that such commercial olefins need not necessarily be purified from same prior to being hydroformylated.

The amount of aldehyde product present in the liquid mediums employable as the starting materials of this invention may range from 0 to about 90 percent by weight or higher of the liquid medium. Such amounts are not narrowly critical and will of course in general merely be dependent upon the particular reaction conditions and efficiency of the hydroformylation process from whence the liquid medium starting materials of this invention may be derived. In general, preferred hydroformylation processes are those capable of producing a hydroformylation reaction product medium containing from about 10 to about 80 percent by weight of aldehyde product. Preferably the amount of aldehyde product present in the liquid medium starting materials employable in this invention may range from 0 to about 80 percent by weight, and more preferably from about 1 to 60 percent by weight, of the liquid medium.

More preferably the liquid medium starting materials of this invention correspond to all or a part of the reaction medium of a hydroformylation process as outlined herein or correspond to all or a part of the liquid catalyst containing recycle medium of such a hydroformylation process (i.e. that liquid catalyst containing residue obtained, after the removal of that desired amount of aldehyde product from the hydroformylation reaction product medium outside of the hydroformylation reactor or hydroformylation zone), which is recycled to the reactor in order to establish a continuous hydroformylation catalyst recycle process.

Of course it is to be further understood that the liquid medium starting materials of this invention may also contain additional ingredients corresponding to those which have either been deliberately employed in the hydroformylation process from which said liquid medium starting materials may be derived or which have been formed in situ during the hydroformylation process. For instance, obviously since an olefin starting material is being hydroformylated, the liquid medium starting materials of this invention may contain some unreacted olefin starting material. The amount of such unreacted olefin present in any said liquid medium starting material will be in general governed by the efficiency of the hydroformylation process. In general amounts of unreacted olefin may range from about 0 to about 20 percent by weight of the liquid medium.

Likewise, minor amounts of in situ type by-products that may be formed during the hydroformylation process may also be correspondingly present in the liquid medium starting materials of this invention, e.g., in situ type by-products derived from the olefinic starting materials, such as unreacted isomerized olefin, hydrogenated olefin e.g., corresponding saturated hydrocarbons or paraffin by-products); in situ type by-products derived from the aldehyde products, such as high boiling aldehyde condensation by-products (as described e.g. in U.S. Pat. No. 4,148,830 and said U.S. Pat. No. 4,247,486 discussed above); and possibly even some in situ type alkyl substituted phosphorus ligand by-product. Further minor amounts of other additional co-solvent type diluents or additives, if employed in the hydroformylation process, e.g., aqueous alkaline or buffer solutions such as may be employed in an aqueous hydroformylation process, may correspondingly be present in the liquid medium starting materials of this invention. Accordingly, it should be sufficient for the purpose of this invention to understand that whatever compounds are present in the hydroformylation reaction medium of the hydroformylation process from which the liquid medium starting material of this invention is derived, may also be correspondingly present in said liquid medium starting materials.

Likewise, the reaction conditions for effecting such hydroformylation processes may be those heretofore conventionally used and may comprise a reaction temperature of from about 45° C. to about 200° C. and pressures ranging from about 1 to 10,000 psia.

The total gas pressure of hydrogen, carbon monoxide and olefinic unsaturated starting compound of such hydroformylation processes may range from about 1 to about 10,000 psia, while it is preferred that the process be operated at a total gas pressure of hydrogen, carbon monoxide and olefinic unsaturated starting compound of less then about 1500 psia and more preferably less than about 500 psia. The partial pressure of the reactants is not particularly critical and depends predominately on the amount and nature of the reactants employed and the desired result to be obtained. For instance, in non-aqueous hydroformylation processes the carbon monoxide partial pressure is preferably from about 1 to about 120 psia and more preferably from about 3 about 90 psia. while the hydrogen partial pressure is preferably about 10 to about 200 psia and more preferably from about 20: to about 160 psia. In general the $H_2$:CO molar ratio of gaseous hydrogen to carbon monoxide may range from about 1:10 to 100:1 or higher, the more preferred hydrogen to carbon monoxide molar ratio being from about 1:1 to about 10:1. Further, it is more preferred to employ a hydroformylation reaction temperature of from about 60° C. to about 140° C. Moreover, the subject invention is especially useful for improving continuous hydroformylation processes.

It is to be further understood that while the subject invention is preferably directed to treating a liquid medium that has been directly obtained from a hydroformylation process, the liquid medium starting materials of this invention also encompass any subsequent liquid medium derived from such an initial liquid medium so obtained, provided said subsequently derived liquid medium also contains at least some amount of each of the three main ingredients defined above i.e., catalyst, the partially deactivated rhodium-tertiary organophosphine complex catalyst, the free tertiary organophosphine ligand and a solvent for said complex catalyst and said free ligand, and more preferably also at least some amount of the aldehyde product.

As noted above the organic reagents employable in Step (1) of the process of this invention can be any such reagent selected from the group consisting of (a) alkyne compounds having the formula $R-C\equiv C-CH_2-X$, (b) alkenes having the formula $(R^1)(R^2)C=C(R^3)-CH_2-X$, (c) diketene, (d) methyl halides, (e) methyl sulfonates, (f) propiolate compounds having the formula $HC\equiv C-C(O)OR^{14}$, and (g) oxide compounds having the formula

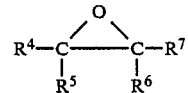

wherein R, $R^1$, $R^2$, $R^3$, $R^4$, $R^5$, $R^6$, $R^7$, $R^{14}$ and X are the same as defined above. More preferably each R, $R^1$, $R^2$, and $R^3$ radical represents hydrogen.

Illustrative monovalent hydrocarbon radicals having from 1 to 18 carbon atoms represented by the $R^1$, $R^2$, $R^3$, $R^4$, $R^5$, $R^6$, $R^7$, and radicals in the above formulae include alkyl radicals such as methyl, ethyl, propyl, butyl, tertiary butyl, hexyl, etc.; aryl radicals such as phenyl, naphthyl, etc.; aralkyl radicals such as phenylethyl, benzyl, etc.; alkaryl radicals such as tolyl, xylyl, etc.; and cycloalkyl radicals, such as cyclohexyl, etc. Preferred monovalent hydrocarbon radicals are those containing from 1 to 8 carbon atoms, and more preferably they are phenyl or alkyl radicals, especially alkyl. Of course it is to be further understood that such hydrocarbon radicals represented by the radicals R through $R^7$ and $R^{14}$ may also be substituted with one or more substitutents that do not unduly adversely affect the desired purpose of this invention. Illustrative substitutents that may be present on such hydrocarbon radicals, in addition of course to additional corresponding hydrocarbon radicals such as alkyl, aryl, aralkyl, alkaryl and cyclohexyl substitutents, may include for example silyl radicals such as $-Si(R^9)_3$; amino radicals such as $-N(R^9)_2$; acyl radicals such as $-C(O)R^9$; acyloxy radicals such as $-OC(O)R^9$; amido radicals such as $-CON(R^9)_2$ and $-N(R^9)COR^9$; sulfonyl radicals such as $-SO_2R^9$; alkoxy radicals such as $-OR^9$; thionyl radicals such as $-SR^9$; phosphonyl radicals such as $-P(O)(R^9)_2$, as well as, halogen, nitro, cyano, trifluoromethyl, hydroxy radicals, and the like, wherein each $R^9$ individually represents the same or different monovalent hydrocarbon radical having the same meaning as defined for R to $R^7$ above, with the proviso that amino substituents such as $-N(R^9)_2$, each $R^9$ taken together can also represent a divalent bridging group that forms a heterocyclic radical with the nitrogen atom, and in amido substituents such as $-C(O)N(R^9)_2$ and $-N(R^9-$ )COR⁹ each R⁹ bonded to N can also be hydrogen. Of course it is to be understood that any substituted or unsubstituted hydrocarbon groups that make up a particular given organic reagent may be the same or different.

Illustrative halide atoms represented by X in the above formulae include chlorine, bromine and iodine, especially chlorine. Illustrative monovalent hydrocarbon radicals having from 1 to 18 carbon atoms represented by $R^8$ in the above formula for X include alkyl radicals, such as methyl, ethyl, propyl, butyl, tertiary butyl, hexyl, etc.; aryl radicals such as phenyl, naphthyl, etc.; aralkyl radicals such as benzyl, phenylethyl, etc.; alkaryl radicals, such as tolyl, xylyl, etc. and cycloalkyl radicals such as cyclohexyl, etc. Preferred monovalent hydrocarbon radicals are those containing from 1 to 8 carbon atoms such as benzyl or phenyl radicals, and more preferably alkyl radicals, especially methyl. Of course it is to be further understood that such hydrocarbon radicals of $R^8$ may also be substituted with one or more substitutents that do not unduly adversely affect the desired purpose of this invention. Illustrative substitutents that may be present on such $R^8$ hydrocarbon radicals, in addition of course to corresponding hydrocarbon radicals such as alkyl, aryl, aralkyl, alkaryl and cyclohexyl substitutents, may include for example silyl radicals such as —Si($R^9$)₃; amino radicals such as —N($R^9$)₂; acyl radicals such as —C(O)$R^9$; acyloxy radicals such as —OC(O)$R^9$; amido radicals such as —CON($R^9$)₂ and —N($R^9$)COR⁹; sulfonyl radicals such as —SO₂$R^9$; alkoxy radicals such as —O$R^9$; thionyl radicals such as —S$R^9$; phosphonyl radicals such as —P(O)($R^9$)₂, as well as, halogen, nitro, cyano, trifluoromethyl, hydroxy radicals, and the like, wherein each $R^9$ individually represents the same or different monovalent hydrocarbon radical having the same meaning as defined for $R^8$ above, with the proviso that amino substituents such as —N($R^9$)₂, each $R^9$ taken together can also represent a divalent bridging group that forms a heterocyclic radical with the nitrogen atom, and in amido substituents such as —C(O)N($R^9$)₂ and —N($R^9$)COR⁹ each $R^9$ bonded to N can also be hydrogen. Preferred substituents include e.g., cyano and —C(O)CH₃.

Illustrative anions represented by Y in the above phosphonium radical formula include halogen e.g., chlorine, bromine, etc.; sulfonic acids; acetic acids; and the like.

Preferred organic reagents are those of the above formulae for said propiolate compounds and said alkyne and alkene compounds wherein X represents a halide, carboxylate or sulfonate radical. Organic reagents such as the above propiolate and oxide compounds, as well as alkyne and alkene compounds wherein X is a carboxylate radical as defined above are more preferred over the other organic reagents defined above. The most preferred organic reagents are the propiolate compounds and the alkyne and alkene compounds defined above, wherein X is a carboxylate radical, especially such alkyne compounds.

Illustrative alkyne compounds that may be employed as the organic reagent of the process of this invention include e.g., propargyl formate, propargyl acetate, propargyl propionate, propargyl butyrate, propargyl cyanoacetate, propargyl acetoacetate, propargyl chloride, propargyl bromide, propargyl iodide, propargyl benzene sulfonate, propargyl triphenylphosphonium bromide, and the like. The prefer compounds are those of the formula RCH≡CCH₂OC(O)$R^8$ wherein R and $R^8$ are the same as defined above, especially propargyl acetate.

Illustrative alkene compounds that may be employed as the organic reagent of the process of invention include e.g. allyl acetate, allyl propionate, allyl butyrate, allyl methacrylate, furfuryl acetate, allyl trifluroacetate, benzyl acetate, allyl chloride, allyl bromide, allyl iodide, allyl benzene sulfonate, allyl cyanoacetate, allyl triphenylphosphonium bromide, and the like. The preferred alkene compounds are those of the formula $R^1R^2C=C(R^3)CH_2-X$ wherein $R^1$, $R^2$, and $R^3$ are the same as defined above and X represents halogen or a carboxylate of the formula —O(CO)$R^8$ wherein $R^8$ is the same as defined above, and more preferably wherein X is a carboxylate, especially allyl acetate.

Illustrative propiolate compounds that may be employed as the organic reagent of the process of this invention include e.g., methyl propiolate, ethyl propiolate, propyl propiolate, butyl propiolate, isobutyl propiolate, pentyl propiolate, hexyl propiolate, phenyl propiolate, and the like. The preferred propiolate compounds are those having the above formula wherein $R^{14}$ represents a monovalent hydrocarbon radical as defined above, especially alkyl. The more preferred propiolate compounds are methyl and ethyl propiolates.

Illustrative methyl halides and methyl sulfonate organic reagents that may be employable in the process of this invention include e.g., methyl chloride, methyl bromide, methyl benzene sulfonate, and the like.

Illustrative oxide compounds that may be employable in the process of this invention, include e.g., cyclohexene oxide, cyclopentene oxide, ethylene oxide, propylene oxide, styrene oxide, and the like.

The diketene organic reagent may be depicted by the formula:

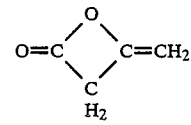

More particularly, the treatment of the liquid medium starting material of this invention (i.e. Step 1, which is conducted under non-hydroformylation conditions, i.e., in the essential absence of syn gas (CO+H₂), can be accomplished by mixing an organic reagent of choice with the desired liquid medium starting material to obtain an organic reagent treated solubilized rhodium-tertiary organophosphine complex product. The manner of said mixing of the organic reagent with the liquid medium starting material and the order of addition is not critical and such can be carried out in any conventional fashion using any suitable equipment and technique, the preferred result merely being a through inclusion of the organic reagent in the liquid medium. In general merely adding the organic reagent to the liquid medium and gently stirring the solution should be sufficient to accomplish the desired result.

Moreover in view of the fact that the subject invention is directed to obtaining at least some improvement, in the hydroformylation activity of the partially deactivated rhodium-tertiary organophosphine complex hydroformylation catalyst contained in the liquid medium to be treated and because the partially deactivated catalysts in said liquid medium starting materials can vary both in terms of their nature and concentrations it is apparent no specific values can be arbitrarily given to such treatment conditions as e.g., the amount of reagent, pressure, temperature and contact time for said treatment that will encompass every given situation. Such conditions can vary greatly and are not narrowly critical and obviously need only be at least sufficient to obtain the result desired. For instance, in some cases a particular organic reagent may be more reactive than another and thus a smaller amount of the more reactive reagent may be beneficial, while in other circumstances a larger amount of the less reactive reagent may prove more desirable. Likewise treatment conditions such as temperature, pressure and contact time may also vary greatly and any suitable combination of such conditions may be employed herein. For instance, a decrease in any one of such conditions may be compensated for by an increase in one or both of the other conditions, while the opposite correlation is also true. In general the organic reagent may be added to and mixed with the liquid medium starting material at liquid temperatures ranging from about 10° C. to about 180° C., while temperatures ranging from about 20° C. to about 130° C. may be suitable in most instances. It is generally preferred to carry out said treatment at atmospheric (ambient) pressure, although higher or lower pressures may be employed if desired. Of course it is obvious that the contact time of the organic reagent and liquid medium involved will be directly related to the particular partially deactivated rhodium-tertiary organophosphine complex catalyst and particular organic reagent involved, as well as to such treatment conditions such as temperature, etc. and such contact time may vary from a matter of minutes to a few hours. Experience will determine the preferred temperature and contact time.

However, said treatment of the liquid medium starting material with the organic reagent according to Step (1) this invention must be under non hydroformylation conditions, which is to say that Step (1) of the process of this invention must be carried out in the essential absence of syn gas (CO+H$_2$), thus preventing any adverse simultaneous hydroformylation of the organic reagent and other compounds present in the liquid medium starting material that is being employed in said Step (1). Preferably said Step (1) is carried out under a nitrogen atmosphere, although mixtures of nitrogen and any other gas (except syngas) may be employed provided they do not unduly adversely affect the desired purpose of this invention. For example, hydrogen may be employed.

Of course the amount of organic reagent employed in Step (1) of this invention need only be that minimum amount necessary to help achieve the desired end result of this invention. In general it is considered that the amount of organic reagent employed may range from about 0.1 up to about 1000 moles or higher per mole of rhodium, calculated as rhodium metal, in the liquid medium starting material, although it is recommended to employ at least one mole of the organic reagent per mole of said rhodium. More preferably it is recommended that an excess molar amount of the organic reagent be employed although no added benefit is seen in employing very large excess amounts and very large excess amounts could be more detrimental than positive. In general it is considered that amounts of organic reagents ranging from about 0.5 to 500 moles per mole of rhodium, calculated as rhodium metal, in the liquid starting material should be sufficient for most purposes, with preferred amounts being from about 1 to about 300 moles per mole of rhodium, calculated as rhodium metal.

In any event it is sufficient for the purpose of this invention to understand that the organic reagent is mixed with the liquid medium starting material in Step (1) of this invention to obtain an organic reagent treated solubilized rhodium-tertiary organophosphine complex product, which in turn can be treated according to Step (2) of this invention to obtain a rhodium-tertiary organophosphine complex hydroformylation catalyst having better catalytic hydroformylation activity than the partially deactivated rhodium-tertiary organophosphine complex hydroformylation catalyst in said liquid medium starting material.

Step 2 of the process of this invention comprises of eliminating from said organic reagent treated solubilized rhodium-tertiary organophosphine complex product of said Step (1), any hydroformylation catalytic inhibitor formed by said Step (1), to obtain a rhodium-tertiary organophosphine complex hydroformylation catalyst that is more catalytically active than said partially deactivated rhodium-tertiary organophosphine complex hydroformylation catalyst in the liquid medium starting material of Step (1) and such may be accomplished in a number of ways.

For instance, while not intending to be held to any specific chemical theory or mechanistic discourse on just exactly how the beneficial desired result of the process of this invention is achieved, it is considered that intrinsic deactivation of the rhodium-tertiary organophosphine catalyst is due at least in part to the in situ formation of rhodium complex clusters during the hydroformylation process, which are catalytically inactive or less active than the active rhodium complex catalyst species, thus decreasing the amount of active rhodium values in the reaction medium. It is further considered that in Step (1) of the process of this invention the organic reagent reacts with the rhodium of such clusters to form new rhodium complex species in the treated liquid medium. While the new rhodium complex species in the organic reagent treated solubilized rhodium-tertiary organophosphine complex product of Step (1) has not been found to immediately exhibit improved catalytic activity over that of the partially deactivated rhodium-tertiary organophosphine complex catalyst in the liquid medium starting material, it is considered that such is due to a catalytic inhibitor formed during the Step (1) treatment. Said catalytic inhibitor is considered to be the acid moiety of the organic reagent which may be present in said treated complex product of Step (1) in its free form and/or as part of the new rhodium complex species formed by the treatment of Step (1). In any event it has been found that the elimination of whatever form catalytic inhibitor is present as, results in obtaining a rhodium-tertiary organophosphine complex hydroformylation catalyst that is more catalytically active than the partially deactivated rhodium-tertiary organophosphine complex hydroformylation catalyst in the liquid medium starting material of the process of this invention. Again while not intending to be held to any specific chemical theory or mechanistic disclosure as to the actual working of this invention, it is considered that during and/or as a result of the elimination of such catalyst inhibitor via Step (2), the organic reagent treated solubilized rhodium complex product of Step (1), is somehow converted from an inhibited complex to an active rhodium complex species. In any event it is sufficient for the purpose of understanding this invention to know that as a result of both Step (1) and Step(2) of the process of this invention, a rhodium-tertiary organophosphine complex hydroformylation catalyst is obtained that is more catalytically active than the partially deactivated rhodium-tertiary organophosphine complex hydroformylation catalyst present in the liquid medium starting material.

Accordingly Step (2) of the process of this invention comprises eliminating from the organic reagent treated solubilized rhodium-tertiary organophosphine complex product of Step (1) any hydroformylation catalytic inhibitor formed by said Step (1) to obtain a rhodium-tertiary organophosphine complex hydroformylation catalyst that is more catalytically active, than the partially deactivated rhodium - tertiary organophosphine complex hydroformylation catalyst in the liquid medium of Step (1).

Said elimination of such a hydroformylation catalytic inhibitor by Step (2) of the process of this invention may comprise either removing or neutralizing said hydroformylation catalytic inhibitor in any suitable manner as described more fully herein below.

For instance, it is to be understood that the particular procedure applicable in Step (2) may be qoverned and/or depend upon such factors as the particular solvent, ligand and activity of the catalyst employed in the liquid medium starting material of Step (1), as well as the organic reagent employed and the desired end use intended for the catalytically improved catalyst.

One illustrative procedure of said Step (2) may comprise removing such catalytic inhibitor formed by Step (1) by contacting an organic reagent treated organic solvent-solubilized rhodium-tertiary organophosphine complex product of Step (1) with any suitable aqueous alkaline or buffer solution and phase separating the organic and aqueous phases of the result mixture to obtain an organic solubilized rhodium-tertiary organophosphine complex hydroformylation catalyst product that is more catalytically active than the organic solubilized partially deactivated rhodium-tertiary organophosphine complex hydroformylation catalyst contained in the liquid medium starting material of Step (1).

Obviously such a procedure which relies upon organic-aqueous phase separation to remove the catalytic inhibitor is suitable only when the partially deactivated rhodium - tertiary organophosphine complex hydroformylation catalyst in the liquid medium starting material of Step (1) is solubilized in an organic solvent, e.g. derived from a non-aqueous hydroformylation process, and wherein the tertiary organophosphine employed is an organic solvent soluble, non-ionic organophosphine, e. ., triphenylphosphine or an ionic organophosphine, which is soluble in an organic solvent, e.g. the sodium salt of 3-(diphenylphosphino) benzene sulfonic acid in N-methylpyrrolidone.

It is considered that this particular procedure of Step (2) will be appropriate regardless of the particular organic reagent employed in Step (1), i.e., any of the above mentioned organic reagents may be employable with this procedure, since it is considered that the catalytic inhibitor formed by Step (1) may be eliminated (removed) along with the aqueous phase during said phase separation. The improvement in hydroformylation catalytic activity of the obtained organic solubilized rhodium - tertiary organophosphine complex product of said phase separation may then be confirmed by employing same in a non-aqueous hydroformylation process. Of course it is to be understood that such confirmation may or may not be immediately obtained upon the start up of such a non-aqueous hydroformylation process but may come about later after the non aqueous hydroformylation has been continuously carried out for a while.

Alternatively when the partially deactivated rhodium-tertiary organophosphine complex hydroformylation catalyst in the liquid medium starting material of Step (1) is solubilized in an aqueous solvent, e.g., derived from an aqueous hydroformylation process and wherein the tertiary organophosphine ligand is an ionic organophosphine, e.g., the salts of a sulfonated triphenylphosphine, which is soluble in an aqueous solvent e.g., water, said Step (2) may comprise eliminating the catalytic inhibitor formed by Step (1) by contacting the organic reagent treated aqueous solubilized rhodium-tertiary ionic organophosphine complex product of Step (1) with any suitable aqueous alkaline or buffer solution and employing same in an aqueous hydroformylation process to obtain an aqueous solubilized rhodium-tertiary ionic organophosphine complex hydroformylation catalyst product that is more catalytically active than the aqueous solubilized partially deactivated rhodium-tertiary ionic organophosphine complex hydroformylation catalyst contained in the liquid medium starting material of Step (1).

It is considered that this particular procedure of Step (2) will be appropriate regardless of the particular organic reagent employed in Step (1), i.e. any of the above mentioned organic reagents may be employable with this procedure, since it is considered that the catalytic inhibitor formed by Step (1) may be eliminated via neutralization due to the aqueous alkaline or buffer solution treatment and that the neutralized inhibitor may remain in the reaction medium of an aqueous hydroformylation process that employs said aqueous alkaline or buffer treated catalyst product without unduly adversely affecting obtaining of the desired catalytically improved aqueous solubilized rhodium-tertiary ionic organophosphine complex hydroformylation catalyst product. Of course it is to be understood that confirmation of such an improvement may or may not be immediately obtained upon the start up of such an aqueous hydroformylation process but may come about later after the aqueous hydroformylation has been continuously carried out for a while.

Yet another and even more preferred procedure of Step (2) merely comprises continuously hydroformylating the organic reagent treated solubilized rhodium-tertiary organophosphine complex product of Step (1) to obtain a solubilized rhodium-tertiary organophosphine complex hydroformylation catalyst product that is more catalytically active than the aqueous solubilized partially deactivated rhodium-tertiary organophosphine complex hydroformylation catalyst contained in the liquid starting material of Step (1). This preferred procedure omits the need for the above discussed treatment with an aqueous alkaline or buffer solution of said product of Step (1) prior to such hydroformylation. However the success of this procedure may be dependent upon the type of organic reagent employed in Step (1) and/or the type of hydroformylation process (aqueous or non aqueous) involved in Step (2). For example it has been found that when the organic reagent of Step (1) is propargyl acetate, continuous non-aqueous hydroformylation of the treated product of Step (1) resulted in a hydroformylation process that exhibited improved catalytic activity above that obtained with the corresponding untreated partially deactivated rhodium - tertiary organophosphine complex catalyst in the liquid medium starting material of Step (1) Accordingly it is considered that the use of mildly acidic organic reagents such as the alkyne and alkene compounds of the above formulae wherein X represents a carboxylate radical, as well as the organic reagent propiolate compounds and oxide compounds defined above, in Step (1) result in a relatively mild catalytic inhibitor which may be conveniently eliminated (removed) via continuous hydroformylation over time.

It is considered that this particular procedure of Step (2) will be appropriate when such mildly acidic organic reagents are employed in Step (1), regardless of the type of solvent (organic or aqueous) and the type of tertiary organophosphine ligand (nonionic or ionic) in the liquid medium starting material of Step (1) as well as regardless of the type of continuous hydroformylation process employed (non aqueous or aqueous) in Step (2) provided of course that such three variables are compatible with each other (e.g., an organic solvent, non ionic or organically soluble ionic ligand and a continuous non-aqueous hydroformylation; or an aqueous solvent, water soluble ionic ligand and a continuous aqueous hydroformylation process). For example it is considered that when such mildly acidic organic reagents are employed the inhibitor formed by Step 1 may be gradually eliminated (removed) from the reaction medium of the continuous hydroformylation process e.g., via the recovery procedure used to obtain the desired aldehyde product thus resulting in the desired catalytically improved rhodium-tertiary organophosphine complex catalyst. Said improvement in catalytic activity may be readily determined by analyzing for same during said continuous hydroformylation. As noted above such confirmation of improved activity may only be exhibited after the hydroformylation has been continuously carried out for a while.

Moreover in the case wherein the procedure of step (2) comprises a continuous aqueous hydroformylation process carried out in an aqueous reaction medium that contains an alkaline or buffer material, it is considered that it may be possible to continuously hydroformylate an organic reagent treated aqueous solubilized rhodium-tertiary ionic organophosphine product of Step (1), regardless of the particular organic reagent employed and without any necessary alkaline or buffer pretreatment, to obtain an aqueous solubilized rhodium-tertiary ionic organophosphine complex hydroformylation catalyst product that is more catalytically active than the aqueous solubilized partially deactivated rhodium-tertiary ionic organophosphine complex hydroformylation catalyst contained in the liquid medium starting material of Step (1 . In this procedure it is considered that any inhibitor formed by Step (1) that is too strongly acidic, e.g., a halide or sulfonic acid type inhibitor, to be eliminated (removed) in the same fashion as discussed above for mildly acidic inhibitors, may be eliminated via neutralization due to the presence of the alkaline or buffer material in the reaction medium of the continuous aqueous hydroformylation process. Of course it is again to be understood that any confirmation of improved activity may only be exhibited after the hydroformylation has been continuously carried out for a while.

Any suitable alkaline material may be employable for the aqueous alkaline solutions useful in any of the above discussed procedures of Step (2). Illustrative alkaline materials that may be mentioned include e.g., the alkali metal and alkaline earth metal and ammonium salts of hydroxides, carbonates, and borohydride, such as sodium bicarbonate, sodium carbonate, sodium hydroxide, potassium hydroxide, lithium hydroxide, cesium hydroxide, barium hydroxide, calcium hydroxide. ammonium hydroxide, sodium borohydride, and the like, especially sodium bicarbonate.

Aqueous buffer containing solutions may also be useful in any of the above discussed procedures of Step 2. Illustrative buffer mixtures include salts of inorganic oxy acids, such as phosphine acid/monobasic phosphate/dibasic phosphate of an alkali metal, boric acid/borate of an alkali metal, and carbonate/bicarbonate of an alkali metal; e.g., equimolar mixtures of the monobasic phosphate and the dibasic phosphate of sodium or of potassium, or of the carbonate and the bicarbonate of sodium or of potassium.

Of course it is to be understood that any suitable mixture of aqueous alkaline and buffer solution may be employed if desired and aqueous hydroformylation process employing such materials are known e.g., as seen by USP 4,248,802.

The contacting of the organic reagent treated rhodium-tertiary organophosphine complex catalyst product of Step (1) and such aqueous alkaline or buffer solutions may be carried out in any suitable manner using any suitable equipment. Such contact may be carried out under non hydroformylating conditions or under aqueous hydroformylation conditions as explained above. For example the contact may be effected under non hydroformylating conditions by simply mixing the aqueous alkaline or buffer solution with the treated liquid solution product of Step (1) such as in a conventional washing procedure, or under aqueous hydroformylation conditions e.g., when the alkaline or buffer material relied upon to achieve the desired result is present in the reaction medium of the aqueous hydroformylation process.

Preferably the subject invention is directed to improving the catalytic activity of a partially deactivated rhodium-tertiary organophosphine complex hydroformylation catalyst that has been derived from a non aqueous hydroformylation process for reuse in the same or similar non-aqueous hydroformylation process. Thus it is preferred to contact, e.g, wash, the treated product of Step (1) with the aqueous alkaline or buffer solution when employed under non hydroformylation conditions an preferably under nitrogen at atmospheric pressure. Non hydroformylating contacting temperatures of from about 20° C. to about 100° C. and more preferably from about 25° C. to about 65° C. should be sufficient for most purposes, although lower or higher temperatures may be employed if desired. Normally the washing can be completed within a matter of minutes, and the organic and aqueous phases phases of the mixture separated in any desired conventional fashion.

The amount of alkaline or buffer material, when employed in any of the above discussed procedures of Step (2), required to obtain the desired result of this invention is not particularly critical for it obviously need only be that amount sufficient to achieve at least some improvement, and naturally more preferably the best improvement, in catalytic activity of the particular partially deactivated rhodium-tertiary organophosphine complex hydroformylation catalyst involved.

In general when employed under non hydroformylating conditions aqueous alkaline or buffer solutions containing from about 0.1 to about 20% by weight of alkaline or buffer material and ranging from about 0.1 to about 1.5 parts by volume per part of treated product of Step (1) should be sufficient for most purposes. Illustrative preferred aqueous alkaline solutions may include from about 0.1 to about 0.5 parts by volume of a 5 to 10 weight percent aqueous sodium bicarbonate solution. Of course it is to be understood that when employed such aqueous alkaline or buffer solution washes could be carried out more than once if desired e.g., successive washings of the preceding obtained organic phases collected via phase separation from the aqueous phase, although it is believed that only one such washing should be sufficient for most purposes. Further as with any such conventional washing procedure, the obtained separated organic phase may be further washed with water one or more times if desired to remove any small amounts of alkaline or buffer material contained in said organic phase. When employed under aqueous hydroformylating conditions, it may be advantageous to employ that amount of alkaline or buffer material which will keep the pH of the aqueous hydroformylation reaction medium from between about 4 to 10.

As described above such aqueous alkaline or buffer treatment procedures for Step (2), either under non hydroformylating conditions or under aqueous hydroformylation conditions may be considered as being necessary for achieving any improvement in catalyst activity for the partially deactivated rhodium-tertiary organophosphine complex hydroformylation catalyst involved, when the organic reagent used in Step (1) is either (i) an alkyne or alkene compound of the above formula wherein X represents either halogen, a sulfonate or phosphonium radical as defined above, (ii) a methyl halide compound or (iii) a methyl sulfonate compound.

Alternatively, when the organic reagent used in Step (1) is an alkyne or alkene compound of the above formula wherein X represents a carboxylate radical, or a propiolate compound or oxide compound as defined above, the preferred procedure of Step (2) of the process of this invention may comprise merely continuously hydroformylating the treated liquid product solution of Step (1) until at least a sufficient amount of the catalytic inhibitor has been eliminated in order to obtain a rhodium-tertiary organophosphine complex hydroformylation catalyst that is more catalytically active than the partially deactivated rhodium-tertiary organophosphine complex hydroformylation catalyst contained in the liquid medium starting material.

Of course it is to be understood that such continuous hydroformylation processes, be they of a non aqueous or aqueous hydroformylation procedure, discussed above as being employable as Step (2) and/or for confirmation of the desired improved catalytic activity of this invention are well known in the art, as seen already herein discussed above and contained in the above mentioned cited references. Accordingly any of such conventional continuous hydroformylation processes and conditions already disclosed and discussed herein may be employed for said Step (2) and/or for confirmation of the desired improved catalytic activity of this invention and such processes and conditions obviously need not be further detailed again.

The exact time period of continuous hydroformylation required before any improvement in catalyst activity may be observed over that of the corresponding partially deactivated rhodium-tertiary organophosphine complex catalyst employed in Step (1) will of course obviously vary depending upon the compounds and processing conditions involved. Thus obviously no arbitrary time period for such an accomplishment can, nor need be assigned for the elimination of the catalytic inhibitor by such continuous hydroformylation. Rather it is sufficient for an understanding of this invention to know that Step (2) of the process of this invention may be accomplished merely by subjecting the treated product solution of Step (1) to continuous hydroformylation for a sufficient period of time until there is evidenced an improvement in the catalytic activity of the process over that obtainable using the corresponding partially deactivated rhodium-tertiary organophosphine complex catalyst of the liquid medium starting material of this invention. In general it is preferred that some improvement in catalyst activity should be evidenced within at least a few hours or earlier. Of course it is to be understood that any improvement in catalyst activity should continue to get better with time until the maximum improvement possible is obtained.

Again the continuous hydroformylation procedures employable as said Step (2) are not critical and any known conventional procedure that achieves the desired result of the process of this invention may be employed. Preferred continuous hydroformylation processes are those involving a liquid catalyst recycle process wherein one need only treat all or a part of the reaction medium or all or part of the liquid catalyst containing recycle medium according to Step (1) of the process of this invention and then continue to employ the same hydroformylation process.

Thus it should be clear that while the selection of the optimum conditions of this invention to achieve the best results will be dependent upon one's experience in the utilization of the subject invention, in view of the disclosure and examples of this specification, only a certain measure of routine experimentation should be necessary in order to ascertain those conditions which are optimum for a given situation. However, it should also be clear that one of the beneficial factors involved in this invention as employed herein is the wide processing latitude that one has in selecting the proper combination of conditions that will be most useful in obtaining or at least best approaching a particular desired result or need.

Further, as pointed out herein the improved regenerated hydroformylation catalytic activity of a rhodium complex catalyst product improved or obtained according to this invention, may be determined by any suitable method such as e.g., by measuring the rates of reaction of the partially deactivated rhodium complex catalyst in the liquid medium starting material of Step (1) and the rhodium complex catalyst product of this invention as compared to the activity of a fresh rhodium complex catalyst employed in the same manner. This effect may be easily determined by carrying out the hydroformylation reactions and by continuously monitoring the rate of hydroformylation. The difference in hydroformylation.rate or difference in catalyst activity) may then be observed in a convenient laboratory time frame.

Thus the process of this invention provides an excellent means for improving the hydroformylation catalytic activity of an intrinsically partially deactivated rhodium-tertiary organophosphine complex hydroformylation catalyst regardless of whether or not an organic non aqueous hydroformylation or an aqueous hydroformylation procedure is involved. Indeed as seen discussed above this invention provides a suitable means for improving such catalytic activity of such a catalyst e.g., by treating all or part of the hydroformylation reaction medium of such a process or all or part of the catalyst complex containing liquid recycle medium of such process.

For instance a particularly preferred and beneficial aspect of this invention may comprise merely stopping a rhodium organophosphine catalyzed continuous hydroformylation reaction which has been conducted in a reaction vessel (reactor) for a period of time sufficient to partially deactivate the catalyst and Step (1) treating, under non hydroformylation conditions, the hydroformylation reactor medium with an appropriate organic reagent while said reaction medium remains in the reactor, and Step (2) thereafter merely restarting the same continuous hydroformylation process to obtain the desired hydroformylation catalyst that is more catalytically active than the partially deactivated catalyst contained in said untreated reaction medium. The hydroformylation reaction can be stopped by any convenient method e.g., by merely stopping the feed of the reactant gases (olefin, carbon monoxide and hydrogen) to the reaction vessel and clearing the recycle lines of the reaction system. The appropriate organic reagent, e.g., propargyl acetate, may then be added to the reaction medium in the reactor in any appropriate manner and mixed therein to complete Step (1). Step (2) of course then merely comprises restarting the hydroformylation process via the readdition of the reactant gases to the reactor at any desired conventional temperature and pressure and continuing the same hydroformylation using said organic reagent treated reaction medium to obtain the desired result of this of this invention. Of course this invention does not require the continuous hydroformylation process to be stopped at all if such is not desired. For example yet another preferred aspect and benefit of this invention comprises Step (1) treating all or part of the liquid catalyst containing recycle medium of a such a continuous hydroformylation process with an appropriate organic reagent and returning the thus treated catalyst containing recycle medium to the reaction medium in the reactor of the continuous hydroformylation process. Such may be accomplished by any suitable method, e.g., drawing off a part of the recycle medium to an appropriate container treating same and returning the treated medium, without any need for stopping or shutting down the continuous hydroformyaltion, said continuing hydroformylation itself becoming Step (2) of this process upon entry of the treated recycle medium to the hydroformylation reaction medium in the reactor. Of course likewise a portion of the hydroformylation reaction medium itself may be withdrawn from the reactor, and also so treated and returned to the reactor in the same fashion, if desired, without stopping or shutting down the continuous hydroformylation.

Further in addition to being readily returnable to the reaction medium of the same hydroformylation process from whence the partially deactivated rhodium-tertiary organophosphine complex catalyst starting materials of Step (1) may be derived, if desired the improved rhodium-tertiary organophosphine complex product of this invention may be useful as the catalytic starting material or as a catalytic booster for any different conventional hydroformylation process if desired.

The following examples are illustrative of the present invention and are not to be regarded as limitative. It is to be understood that all parts, percentages and proportions referred to herein and in the appended claims are by weight unless otherwise indicated.

The mini reactor activities of Examples 1 to 17 were determined in a small batch, hydroformylation reactor operated at a temperature of about 100° C. and a pressure of about 90–95 psia with a feed mixture of an equimolar amount of propylene, carbon monoxide and hydrogen.

EXAMPLES 1 to 14

This example illustrates improving the hydroformylation catalytic activity of a partially deactivated rhodium - triphenylphosphine complex hydroformylation catalyst composition that had been employed in a non aqueous hydroformylation process directed to producing butyraldehyde by hydroformylating propylene and whose catalytic activity had declined from 100% active to about 85 percent of fresh catalyst.

Each experiment was conducted in essentially the same manner, the treatments being carried out in standard laboratory glassware and under an inert nitrogen atmosphere.

The procedure employed consisted of adding various amounts of the chemical reagents reported in the table below to individual 25 gram samples of said rhodium triphenylphosphine complex catalyst composition consisting essentially of about 12 weight percent triphenylphosphine (TPP) ligand and about 272 ppm rhodium, calculated as rhodium metal, the remainder being essentially butyraldehyde product (about 75–80 weight percent) and hydroformylation by products. About 25 grams of dioctylphthalate (DOP) was also added to each treated catalyst solution mixture to facilitate stripping of the butyraldehyde and other lights, and to allow for a more consistent continuous single pass reactor operation. Each solution mixture was then warmed to about 60° C. for about 4 hours and essentially all of the butyraldehye lights were nitrogen stripped from the solution. Each solution was then added to a single pass reactor and employed in a continuous single pass hydroformylation process directed to hydroformylating propylene (at about 100° C. using a gaseous mixture of about 100 psig. hydrogen, about 18 psig. carbon monoxide and about 23 psig. propylene) for from about 16 to about 28 hours. The catalyst solutions were then discharged from the glass reactor and their catalytic activity determined in a mini reactor. About one cc of a 10 weight percent aqueous sodium bicarbonate solution was then mixed with about 15 cc's of each catalyst solution and the catalytic activity of such organic one phase solutions redetermined in the mini-reactor. The results of each experiment as compared to the activity of fresh catalyst and the initial partially deactivated catalyst are given in the following Table 1.

TABLE 1

| Ex. No. | Reagent | Reagent/ Rhodium[a] | Activity Before[b] | Activity After[c] |
|---|---|---|---|---|
| 1 | None | (Fresh Catalyst) | 100 | 100 |
| 2 | None | (Spent Catalyst)[d] | 83 | 83 |
| 3 | Allyl Chloride | 4.98 | 0 | 95 |
| 4 | Propargyl Benzene Sulfonate | 10.04 | 34 | 107 |
| 5 | Propargyl Chloride | 10.13 | 0 | 95 |
| 6 | Furfuryl Acetate | 10.75 | 80 | 90 |
| 7 | Allyl Methacrylate | 10.00 | 74 | 94 |
| 8 | Benzyl Acetate | 9.92 | 44 | 75 |

TABLE 1-continued

| Ex. No. | Reagent | Reagent/ Rhodium[a] | Activity Before[b] | Activity After[c] |
|---|---|---|---|---|
| 9 | Cyclohexene Oxide | 10.04 | 56 | 95 |
| 10 | Cyclopentene Oxide | 10.00 | 80 | 96 |
| 11 | Diketene | 10.08 | 69 | 74 |
| 12 | Propargyl Triphenylphosphonium Bromide | 9.89 | 0 | 91 |
| 13 | Allyl Trifluoroacetate | 9.82 | 0 | 74 |
| 14 | Ethyl Propiolate | 10.0 | 69 | 97 |

[a] Reagent to Rhodium Molar Ratio.
[b] Mini-reactor activity of treated solution after return from glass reactor.
[c] Mini-reactor activity of treated solution in presence of sodium bicarbonate after return from glass reactor.
[d] Initial partially deactivated untreated catalyst starting material.

Only Example 8, 11 and 13 did not result in an improvement in the catalytic activity of the partially deactivated untreated catalyst starting material.

EXAMPLES 15 to 17

This example illustrates improving the hydroformylation catalytic activity of a partially deactivated rhodium ionic phosphine complex hydroformylation catalyst composition. The ionic phosphine was 3-(diphenylphosphino)-benzene sulfonic acid, sodium salt (TPPMS-Na). The catalyst composition used in Example 15 consisted essentially of about 10 weight percent TPPMS-Na and about 500 ppm of rhodium, calculated as rhodium metal and added as rhodium dicarbonylacetylacetonate, the remainder being about a 50:50 wt. % mixture of Texanol ® and methanol solvent. The catalyst composition used in Example 16 and 17 consisted essentially of a rhodium-TPPMS-Na complex hydroformylation catalyst that had been derived from a continuous non-aqueous hydroformylation process directed to producing tridecanal by hydroformylating dodecene. Said catalyst was an organic one-phase solution consisting essentially of about 7 weight percent TPPMS-Na and 538 ppm rhodium, calculated as rhodium metal, the remainder being about 47 wt. %, N-methylpyrrolidone; about 40 wt. % Texanol ®; 4 wt. % water and about 2 wt. % tridecanal and hydroformylation by-products.

The catalyst compositions used in Examples 15 to 17 were then severely deactivated by exposure to about 50 psi of syn gas (CO+H$_2$ at 100° C. in the absence of any added olefin, for about 24 hours for Example 15 and for about 48 hours for Examples 16 and 17 The catalytic activity of each catalyst composition so deactivated was then determined in a mini reactor.

Each catalyst composition was then treated in essentially the same manner, the treatments being carried out in standard laboratory glassware and under an inert nitrogen atmosphere.

The procedure employed consisted of adding various amounts of the chemical reagents reported in the table below to individual 25 gram samples of the severely deactivated catalyst compositions and warming each solution to the temperature and for the time period stated in the following table. Then about 1 ml. of a 10 weight percent aqueous sodium bicarbonate solution was added to about 15 ml. of each catalyst solution and the catalytic activity of such organic one phase solutions redetermined in a mini reactor. The results of each experiment as compared to the activity of fresh catalyst are given in the following Table 2.

TABLE 2

| Ex. No. | Reagent | Reagent (grams) | Catalyst Solution (grams) | Time (Hrs.) | Temp. (°C.) | Activity Before[a] | Activity After[b] |
|---|---|---|---|---|---|---|---|
| 15 | Allyl Chloride | 0.05 | 15 | 16 | 100 | 43 | 88 |
| 16 | Allyl Chloride | 0.1 | 15 | 48 | 60 | 38 | 100 |
| 17 | Allyl Bromide | 0.1 | 15 | 48 | 60 | 38 | 65 |

[a] Mini-reactor activity of severly deactivated catalyst before treatment.
[b] Mini-reactor activity after treatment of severly deactivated catalyst in the presence of sodium bicarbonate.

Each of the following Examples 18 to 25 employed a sample of a catalyst solution derived from a continuous non-aqueous hydroformylation process directed to producing butyraldehyde from propylene using a rhodium-TTP complex catalyst, which had been operated for a sufficient period of time to cause intrinsic deactivation of the catalyst; i.e., to about 30% of a fresh catalyst [Example 18 and 19] and to about 42% of a fresh catalyst [Example 20 to 25]. The partially deactivated catalyst solutions employed in Examples 18 and 19 contained about 750 ppm rhodium, calculated as rhodium metal, about 22 wt. % triphenylphosphine (TPP) and about 11 wt. % butyraldehyde product, the remainder being hydroformylation by-products, e.g., aldehyde condensation by products. The partially deactivated catalyst solution employed in Examples 20 to 25 contained about 450 ppm rhodium, calculated as rhodium metal, about 12 wt. % triphenylphosphine (TPP) and about 14 wt. % butyraldehyde, the remainder being hydroformylation by products, e.g., aldehyde condensation by products.

Moreover, each of Examples 18 to 25 employed the following non-aqueous continuous hydroformylation procedure to reactivate the partially deactivated catalyst and demonstrate the improved catalytic activity that can be obtained by this invention.

The untreated catalyst solution was charged to a continuously operating single pass hydroformylation reactor. A mixture of carbon monoxide, hydrogen, propylene and nitrogen was fed to the reacting system. The reactor was heated to 100° C. and a steady state mixture of reactant gases (i.e., syn gas and propylene) was obtained in the system (carbon monoxide about 18 psig; hydrogen, about 95 psig; propylene about 23 psig). Total reaction pressure was about 160 psig. The butyraldehyde production rates, in gram moles per liter per hour, were determined by monitoring the flow rate and composition of off gases from the reactor.

Once a stable production rate had been achieved, e.g., over a 42 to 86 hour time period, the reacting gases were valved off to the reactor and the prescribed amount of organic reagent was added to the solution contained in the reactor and in the absence of said reactant gases. The contents of the reactor were held at temperature under an a nitrogen atmosphere, unless otherwise specified. After a period of time believed to be sufficient to permit significant contact between the rhodium complex and organic reagent to occur, the reacting gases i.e., syn as and propylene, were re introduced to the reactor establishing the previously achieved reaction conditions. Upon re introduction of the gases continued monitoring of the aldehyde production rates was accomplished.

Control experiments were conducted for the Examples. In the control experiments freshly prepared catalyst solution o similar composition was placed in the reactor and its operating performance determined. Net catalyst activities for the partially deactivated and catalytically improved catalyst solutions were determined by comparison to the fresh solution. Although in most cases the initial catalyst activity after treatment was less than that prior to said treatment, in each case the activity of the catalyst solution eventually increased to a level greater than the pre treatment level.

EXAMPLE 18

20 ml of deactivated catalyst solution (described above) was charged to a continuously operating hydroformylation reactor. The initial rate (1.25 gram mols/liter/hour) and catalyst activity (about 30% of fresh catalyst) was determined over 42 hours. After the reactant gases were valved off to the reactor, propargyl acetate (about 50 equivalents based on the total rhodium content) was added to the catalyst solution and the treated solution was held at 100° C. and under 160 psig of nitrogen for 16 hours. The reactant gases were then turned back on and the hydroformylation rate and the catalyst activity monitored over 19 hours of continuous hydroformylation. The hydroformylation rate and the catalyst activity gradually increased from 0 to about 66 percent of fresh catalyst as seen reported in the following Table 3.

TABLE 3

| Run Time (HRS) | Rate (g-mol/L/Hr) | Catalyst Activity (% of fresh Catalyst) |
|---|---|---|
| 0.0 | 0.0 | 0.0 |
| 4 | 1.68 | 31.4 |
| 9 | 1.75 | 42.4 |
| 15 | 2.00 | 61.4 |
| 19 | 2.20 | 66.4 |

EXAMPLE 19

20 ml of deactivated catalyst solution described above) was charged to a continuously operating hydroformylation reactor. The initial rate (1.10 gram mols/liter/hour) and catalyst activity (about 30% of fresh catalyst) was determined over 46 hours. After the reactant gases were valved off to the reactor, propargyl acetate (about 100 equivalents based on the total rhodium content) was added to the catalyst solution and the treated solution was held at 100° C. and under 160 psig of nitrogen for 16 hours. The reactant gases were then turned back on and the hydroformylation rate and the catalyst activity monitored over 54 hours of continuous hydroformylation. The hydroformylation rate and the catalyst activity gradually increased from 0 to about 88 percent of fresh catalyst as seen reported in the following Table 4.

TABLE 4

| Run Time (HRS) | Rate (g-mole/L/Hr) | Catalyst Activity (% of fresh catalyst) |
|---|---|---|
| 0.0 | 0.0 | 0.0 |
| 4.7 | 1.08 | 28.3 |
| 9.0 | 1.85 | 51.3 |
| 12.7 | 2.01 | 57.0 |
| 16.0 | 2.13 | 60.7 |
| 19.7 | 2.19 | 65.4 |
| 23.0 | 2.27 | 66.3 |
| 30.4 | 2.31 | 75.0 |
| 42.4 | 2.56 | 83.3 |
| 54.4 | 2.63 | 87.5 |

EXAMPLE 20

20 ml of deactivated catalyst solution (described above) was charged to a continuously operating hydroformylation reactor. The initial rate 1.49 gram mols/liter/hour) and catalyst activity (about 52% of fresh catalyst) was determined over 80 hours. After the reactant gases were valved off to the reactor, propargyl acetate (about 100 equivalents based on the total rhodium content) was added to the catalyst solution and the treated solution was held at 70° C. and under 60 psig of nitrogen and 100 psig of hydrogen for 16 hours. The reactant gases were then turned back on and the hydroformylation rate and the catalyst activity monitored over 13 hours of continuous hydroformylation. The hydroformylation rate and the catalyst activity gradually increased from 0 to about 81 percent of fresh catalyst as seen reported in the following Table 5.

TABLE 5

| Run Time (HRS) | Rate (g-mol/L/Hr) | Catalyst Activity (% of fresh Catalyst) |
|---|---|---|
| 0.0 | 0.0 | 0.0 |
| 2.1 | 0.82 | 24.1 |
| 5.5 | 1.33 | 43.2 |
| 9.2 | 1.74 | 66.8 |
| 12.5 | 2.07 | 80.5 |

EXAMPLE 21

20 ml of deactivated catalyst solution (described above) was charged to a continuously operating hydroformylation reactor. The initial rate (1.42 gram-mols/liter/hour) and catalyst activity (about 42% of fresh catalyst) was determined over 83 hours. After the reactant gases were valved off to the reactor, propargyl cyanoacetate (about 35 equivalents based on the total rhodium content) was added to the catalyst solution and the treated solution was held at 70° C. and under 160 psig of nitrogen for 16 hours. The reactant gases were then turned back on and the hydroformylation rate and the catalyst activity monitored over 5 hours of continuous hydroformylation. The hydroformylation rate and the catalyst activity gradually increased from 0 to 61 percent of fresh catalyst as seen reported in the following Table 6

TABLE 6

| Run Time (HRS) | Rate (g-mol/L/Hr) | Catalyst Activity (% of fresh Catalyst) |
|---|---|---|
| 0.0 | 0.0 | 0.0 |
| 1.4 | 0.41 | 11.2 |
| 5.1 | 1.91 | 61.2 |
| 8.4 | 2.00 | 62.8 |
| 12.1 | 1.89 | 59.6 |
| 15.4 | 1.95 | 61.2 |

EXAMPLE 22

20 ml of deactivated catalyst solution (described above) was charged to a continuously operating hydroformylation reactor. The initial rate 1.22 gram mols/liter/hour) and catalyst activity (about 42% of fresh catalyst) was determined over 84 hours. After the reactant gases were valved off to the reactor, propargyl acetate (about 100 equivalents based on the total rhodium content) and acetic acid 10 equivalents based on the total rhodium content was added to the catalyst solution and the treated solution was held at 70° C. and under 160 psig of nitrogen for 16 hours. The reactant gases were then turned back on and the hydroformylation rate and the catalyst activity monitored over 16 hours of continuous hydroformylation. The hydroformylation rate and the catalyst activity gradually increased from 0 to 64 percent of fresh catalyst as seen reported in the following Table 7.

TABLE 7

| Run Time (HRS) | Rate (g-mol/L/Hr) | Catalyst Activity (% of fresh Catalyst) |
| --- | --- | --- |
| 0.0 | 0.0 | 0.0 |
| 2.0 | 0.71 | 19.2 |
| 5.3 | 1.3 | 40.4 |
| 9.0 | 1.65 | 51.6 |
| 12.4 | 1.86 | 58.8 |
| 16.1 | 2.02 | 63.6 |

EXAMPLE 23

20 ml of deactivated catalyst solution (described above) was charged to a continuously operating hydroformylation reactor. The initial rate 1.25 gram mols/liter/hour) and catalyst activity (about 40% of fresh catalyst) was determined over 42 hours. After the reactant gases were valved off to the reactor, propargyl acetate (about 100 equivalents based on the total rhodium content) was added to the catalyst solution and the treated solution was held at 100° C. and under 160 psig of nitrogen for 1 hour. The reactant gases were then turned back on and the hydroformylation rate and the catalyst activity monitored over 23 hours of continuous hydroformylation. The hydroformylation rate and the catalyst activity gradually increased from 0 to 87 percent of fresh catalyst as seen reported in the following Table 8.

TABLE 8

| Run Time (HRS) | Rate (g-mol/L/Hr) | Catalyst Activity (% of fresh Catalyst) |
| --- | --- | --- |
| 0.0 | 0.0 | 0.0 |
| 3.1 | 0.79 | 19.5 |
| 6.4 | 1.18 | 42.3 |
| 12.5 | 1.88 | 55.2 |
| 19.5 | 2.09 | 74.5 |
| 23.3 | 2.19 | 87.3 |
| 26.6 | 2.18 | 86.8 |

EXAMPLE 24

20 ml of deactivated catalyst solution (described above) was charged to a continuously operating hydroformylation reactor. The initial rate (1.27 gram mols/liter/hour) and catalyst activity (about 39% of fresh catalyst) was determined over 80 hours. After the reactant gases were valved off to the reactor, propargyl acetate (about 1? ? equivalents based on the total rhodium content) was added to the catalyst solution and the treated solution was held at 100° C. and under 16psig of nitrogen for 16 hours. The reactant gases were then turned back on and the hydroformylation rate and the catalyst activity monitored over 20 hours of continuous hydroformylation. The hydroformylation rate and the catalyst activity gradually increased from 0 to 67 percent of fresh catalyst as seen reported in the following Table 9.

TABLE 9

| Run Time (HRS) | Rate (g-mol/L/Hr) | Catalyst Activity (% of fresh Catalyst) |
| --- | --- | --- |
| 0.0 | 0.0 | 0.0 |
| 2.3 | 0.1 | 2.9 |
| 5.6 | 1.34 | 41.7 |
| 9.3 | 1.64 | 50.8 |
| 13.0 | 1.79 | 57.1 |
| 16.3 | 1.91 | 61.3 |
| 20.0 | 2.08 | 67.1 |

EXAMPLE 25

20 ml of deactivated catalyst solution (described above) was charged to a continuously operating hydroformylation reactor. The initial rate (1.48 gram mols/liter/hour) and catalyst activity (about 35% of fresh catalyst) was determined over 86 hours. After the reactant gases were valved off to the reactor, propargyl propionate (about 100 equivalents based on the total rhodium content) was added to the catalyst solution and the treated solution was held at 100° C. and under 160 psig of nitrogen for 21 hours. The reactant gases were then turned back on and the hydroformylation rate and the catalyst activity monitored over 30 hours of continuous hydroformylation. The hydroformylation rate and the catalyst activity gradually increased from 0 to 55 percent of fresh catalyst as seen reported in the following Table 10.

TABLE 10

| Run Time (HRS) | Rate (g-mol/L/Hr) | Catalyst Activity (% of fresh Catalyst) |
| --- | --- | --- |
| 0.0 | 0.0 | 0.0 |
| 2.5 | 0.68 | 15.4 |
| 6.3 | 1.18 | 27.5 |
| 9.6 | 1.4 | 34.3 |
| 13.3 | 1.53 | 37.5 |
| 19.4 | 1.9 | 44.3 |
| 23.1 | 1.99 | 50.7 |
| 26.4 | 2.06 | 53.8 |
| 30.1 | 2.13 | 55.0 |

Various modifications and variations of this invention will be obvious to a worker skilled in the art and it is to be understood that such modifications and variations are to be included within the purview of this application and the spirit and scope of the appended claims.

What is claimed is:

1. A process for improving the catalytic activity of a partially deactivated solubilized rhodium-tertiary organophosphine complex hydroformylation catalyst, which comprises (1) mixing under non hydroformylating conditions, a liquid medium containing said solubilized partially deactivated complex catalyst, with an organic reagent selected from the group consisting of (a) alkyne compounds having the formula R—C≡C CH$_2$—X, (b) alkene compounds having the formula (R$^2$)C=C(R$^3$)—CH$_2$X, (c) diketene, (d) methyl halides, (e) methyl sulfonates, (f) propiolate compounds having the formula HC≡C—(O)OR$^{14}$ and (g) oxide compounds having the formula

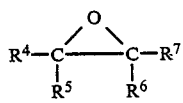

wherein X represents a radical selected from the group consisting of halogen atoms, a carboxylate radical of the formula $-OC(O)R^8$, a sulfonate radical of the formula $-OSOphd\ 2R^8$ a a phosphonium radical of the formula $[-,^-(R^8)_3][Y-]$ wherein $R^8$ in the above formulae for X, each individually represent a monovalent hydrocarbon radical having from 1 to 18 carbon atoms selected from the group consisting of alkyl, aryl, aralkyl, alkaryl and cycloalkyl radicals and wherein Y represents an acid anion; and wherein each R, $R^1$, $R^2$, $R^3$, $R^4$, $R^5$, $R^6$, $R^7$, and $R^{14}$ radical individually represents hydrogen or a monovalent hydrocarbon radical having from 1 to 18 carbon atoms selected from the group consisting of alkyl, aryl, alkaryl, aralkyl and cycloalkyl radicals; with the following provisos: that $R^8$ in the above carboxylate formula can also be hydrogen; that $R^2$ and $R^3$ in the above formula for the alkene compounds can also be bonded together to form a five or six membered heterocyclic ring or monocyclic hydrocarbon ring along with the C=C group shown in said formula; and wherein any two of said $R^4$, $R^5$, $R^6$ and $R^7$ groups in the above formula for the oxides can be bonded together to form a five or six membered monocyclic hydrocarbon ring along with the C—C group shown in said formula; to obtain an organic reagent treated solubilized rhodium-tertiary organophosphine complex product; and (2) eliminating from said product, any hydroformylation catalytic inhibitor formed by said Step (1), to obtain a rhodium-tertiary organophosphine complex hydroformylation catalyst that is more catalytically active than said partially deactivated rhodium-tertiary organophosphine complex hydroformylation catalyst.

2. A process as defined in claim 1, wherein Step (2) comprises contacting said organic reagent treated solubilized rhodium-tertiary organophosphine complex product of Step (1) with an aqueous alkaline or buffer solution, under non-hydroformylation conditions, and separating the organic phase from the aqueous phase of said aqueous alkaline or buffer solution treatment.

3. A process as defined in claim 2 wherein the organic reagent is an alkyne compound having the above defined formula and wherein X represents a radical selected from the group consisting of halogen, and a carboxylate radical having the above formula.

4. A process as defined in claim 3 wherein R represents hydrogen.

5. A process as defined in claim 4 wherein X represents a carboxylate radical.

6. A process as defined in claim 4 wherein X represents a halogen atom.

7. A process as defined in claim 5 wherein the organic reagent is selected from the group consisting of propargyl acetate, propargyl cyanoacetate and propargyl propionate.

8. A process as defined in claim 7, wherein the tertiary organophosphine is triphenylphosphine or the sodium salt of 3 (diphenylphosphino) benzene sulfonic acid.

9. A process as defined in claim 2, wherein the organic reagent is an alkene compound having the above formula and wherein X represents a radical selected from the group consisting of halogen, a carboxylate radical having the above formula and a sulfonate radical having the above formula.

10. A process as defined in claim 9, wherein $R^1$, $R^2$ and $R^3$ each represent hydrogen.

11. A process as defined in claim 10, wherein X represents a halogen atom.

12. A process as defined in claim 10, wherein X represents a carboxylate radical.

13. A process as defined in claim 12, wherein the tertiary organophosphine is triphenylphosphine or the sodium salt of 3 (diphenylphosphino) benzene sulfonic acid.

14. A process as defined in claim 1, wherein Step (2) comprises employing said organic reagent treated solubilized rhodium-tertiary organophosphine complex product of Step (1) in a continuous non-aqueous hydroformylation process and wherein organic reagent is a propiolate compound or alkyne or alkene compound having the above formulae and wherein X represents a carboxylate radical having the above formulae.

15. A process as defined in claim 14, wherein the organic reagent is an alkyne compound and wherein represents hydrogen or an alkyl radical.

16. A process as defined in claim 15, wherein R represents hydrogen.

17. A process as defined in claim 16, wherein the organic reagent is selected from the group consisting of propargyl acetate, propargyl cyanoacetate, and propargyl propionate.

18. A process as defined in claim 17, wherein the tertiary organophosphine is triphenylphosphine or the sodium salt of 3-(diphenylphosphino) benzene sulfonic acid.

19. A process as defined in claim 18, wherein the organic reagent is propargyl acetate.

20. A process as defined in claim 14, wherein Step (1) is carried out under nitrogen.

21. A process as defined in claim 1, wherein Step (2) comprises employing said organic reagent treated solubilized rhodium-tertiary organophosphine complex product of Step (1) in a continuous aqueous hydroformylation process the reaction medium of which contains an aqueous solubilized alkaline or buffer material, and wherein the tertiary organophosphine is an ionic tertiary organophosphine that is soluble in water.

22. A process as defined in claim 14, wherein the liquid medium starting material of step (1) comprises all or part of the hydroformylation hydroformylation medium of a continuous non-aqueous 23. A process as defined in claim 22, wherein Step (1) is carried out in the hydroformylation reactor from whence said hydroformylation reaction medium is obtained.

24. A process as defined in claim 14, wherein the liquid medium starting material of Step (1) comprises all or a part of the liquid catalyst containing recycle medium of a continuous non-aqueous hydroformylation process.

25. A process as defined in claim 2 wherein the organic reagent is a propiolate compound having the above formula.

26. A process as defined in claim 25 wherein $R^{14}$ represents a phenyl radical or an alkyl radical.

27. A process as defined in claim 26 wherein the organic reagent is ethyl propiolate.

28. A process as defined in claim 14 wherein the organic reagent is a propiolate compound having the above formula.

* * * * *

UNITED STATES PATENT AND TRADEMARK OFFICE
CERTIFICATE OF CORRECTION

PATENT NO. : 4,861,918
DATED : August 29, 1989
INVENTOR(S) : D. J. Miller et al.

Page 1 of 2

It is certified that error appears in the above-identified patent and that said Letters Patent is hereby corrected as shown below:

Column 29, line 3, that portion reading "syn as" should read -- syn gas --.

Column 29, line 10, that portion reading "o similar" should read -- of similar --.

Column 31, line 66, that portion reading "about 1??" should read -- about 100 --.

Column 32, line 1, that portion reading "16 psig" should read -- 160 psig --.

Column 32, line 65, that portion reading "$(R^2)C=C(R^3)-CH_2X$" should read -- $(R^1)(R^2)C=C(R^3)-CH_2-X$ --.

Column 32, line 67, that portion reading "$HC\equiv C-(O)OR^{14}$" should read -- $HC\equiv C-C(O)OR^{14}$ --.

Column 33, line 10, that portion reading "$OSOphd2R^8a$" should read -- $-OSO_2R^8$ and --.

Column 33, line 11, that portion reading "$[-,-(R^8)_3][Y-]$" should read -- $[-P^+(R^8)_3][Y-]$ --

Column 33, line 63 and Column 34, line 11, that portion reading "3 (diphenylphosphino)" should read -- 3-(diphenylphosphino) --.

UNITED STATES PATENT AND TRADEMARK OFFICE
CERTIFICATE OF CORRECTION

PATENT NO. : 4,861,918

DATED : August 29, 1989

INVENTOR(S) : D. J. Miller et al.

Page 2 of 2

It is certified that error appears in the above-identified patent and that said Letters Patent is hereby corrected as shown below:

Column 34, line 47, that portion reading "hydroformylation hydroformylation" should read -- hydroformylation reaction --.

Column 34, line 48, add after "non-aqueous", -- hydroformylation process --.

Signed and Sealed this

Fourth Day of December, 1990

Attest:

HARRY F. MANBECK, JR.

Attesting Officer

Commissioner of Patents and Trademarks